(12) United States Patent
Gao et al.

(10) Patent No.: US 7,510,837 B2
(45) Date of Patent: Mar. 31, 2009

(54) SAMPLE PREPARATION METHOD INCORPORATING AN ALKALINE SHOCK

(75) Inventors: Kui Gao, San Diego, CA (US); Michael M. Becker, San Diego, CA (US); Wen Wu, Carlsbad, CA (US); Jeffrey M. Linnen, Poway, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 11/356,613

(22) Filed: Feb. 17, 2006

(65) Prior Publication Data

US 2006/0188912 A1    Aug. 24, 2006

Related U.S. Application Data

(60) Provisional application No. 60/654,199, filed on Feb. 18, 2005, provisional application No. 60/669,192, filed on Apr. 6, 2005.

(51) Int. Cl.
*C12Q 1/68* (2006.01)

(52) U.S. Cl. ........................................................ 435/6

(58) Field of Classification Search ................ 435/9.1, 435/91.2, 6
See application file for complete search history.

(56) References Cited

U.S. PATENT DOCUMENTS

| | | | |
|---|---|---|---|
| 4,868,105 | A | 9/1989 | Urdea et al. |
| 4,965,188 | A | 10/1990 | Mullis et al. |
| 5,118,801 | A | 6/1992 | Lizardi et al. |
| 5,124,246 | A | 6/1992 | Urdea et al. |
| 5,130,238 | A | 7/1992 | Malek et al. |
| 5,283,174 | A | 2/1994 | Arnold, Jr. et al. |
| 5,312,728 | A | 5/1994 | Lizardi et al. |
| 5,399,491 | A | 3/1995 | Kacian et al. |
| 5,437,990 | A | 8/1995 | Burg et al. |
| 5,455,166 | A | 10/1995 | Walker |
| 5,472,840 | A | 12/1995 | Stefano |
| 5,554,516 | A | 9/1996 | Kacian et al. |
| 5,639,604 | A | 6/1997 | Arnold, Jr. et al. |
| 5,656,207 | A | 8/1997 | Woodhead et al. |
| 5,658,737 | A | 8/1997 | Nelson et al. |
| 6,066,455 | A | 5/2000 | Kruse-Mueller et al. |
| 6,682,884 | B2 | 1/2004 | Sharma et al. |
| 6,709,812 | B1 | 3/2004 | Stuyver et al. |
| 2003/0073830 | A1* | 4/2003 | Heath et al. ................ 536/25.4 |
| 2004/0029111 | A1 | 2/2004 | Linnen et al. |

FOREIGN PATENT DOCUMENTS

| | | |
|---|---|---|
| EP | 0 525 882 A1 | 2/1993 |
| EP | 0 611 157 A2 | 8/2006 |
| WO | 88/10315 A1 | 12/1988 |
| WO | 93/22461 A1 | 11/1993 |
| WO | 94/03472 A1 | 2/1994 |
| WO | 95/03430 A1 | 2/1995 |
| WO | 88/01302 A1 | 12/1995 |
| WO | 00/66783 A2 | 11/2000 |
| WO | 03/106714 A1 | 12/2003 |

OTHER PUBLICATIONS

Bej et al. Molecular and Cellular Probes, vol. 4, pp. 353-365, 1990.*
Cassinelli, Mary Ellen. NIOSH Manual of Analytical Methods, Fourth Edition, vol. 7401, Issue 2, pp. 1-4, Aug. 15, 1994.*
Boom et al., "Rapid Purification of Hepatitis B Virus DNA from Serum", J. Clin Microbiol., 1991, 29(9):1804-1811, ASM, Washington, D.C., USA.
Kaneko et al., "Rapid and Sensitive Method for the Detection of Serum Hepatitis B Virus DNA Using the Polymerase Chain Reaction Technique", J. Clin Microbiol., 1989, 27(9):1930-1933, ASM, Washington, D.C., USA.
Lizardi et al., "Exponential Amplification of Recombinant—RNA Hybridization Probes", BioTechnology, 1988, 6:1197-1202, Nature Publications Group, Macmillan Pub. Ltd., GB.
Sambrook et al. Molecular Cloning A Laboratory Manual 2nd ed. (Cold Spring Harbor Laboratory Press Cold Spring Harbor NY 1989) at §§ 1.90-1.91 7.37-7.57 9.47-9.51 and 11.47-11.57 particularly at §§ 9.50-9.51 11.12-11.13 11.45-11.47 and 11.55-11.57.

* cited by examiner

*Primary Examiner*—Gary Benzion
*Assistant Examiner*—Cynthia B Wilder
(74) *Attorney, Agent, or Firm*—Michael J. Gilly

(57) ABSTRACT

Method of preparing a biological sample appropriate for use in a subsequent in vitro nucleic acid amplification reaction. The method involves a rapid, transient exposure to alkaline conditions which can be achieved by mixing an alkaline solution with a pH-buffered solution that includes a detergent and the biological sample to be tested for the presence of particular nucleic acid species using in vitro amplification. The invented method advantageously can improve detection of some target nucleic acids without substantially compromising detectability of others. The method is particularly useful for simultaneously preparing RNA and DNA templates that can be used in multiplex amplification reactions.

38 Claims, 5 Drawing Sheets

SAMPLE PREPARATION METHOD INCORPORATING AN ALKALINE SHOCK

RELATED APPLICATIONS

This application claims the benefit of U.S. Provisional Application No. 60/654,199, filed Feb. 18, 2005, and U.S. Provisional Application No. 60/669,192, filed Apr. 6, 2005. The disclosures of these prior applications are hereby incorporated by reference.

FIELD OF THE INVENTION

The present invention relates to nucleic acid amplification technology. More specifically, the invention relates to a method of preparing a sample preliminary to conducting an in vitro nucleic acid amplification reaction.

BACKGROUND OF THE INVENTION

In vitro nucleic acid amplification techniques are now commonly used for synthesizing, and perhaps detecting vanishingly small quantities of a nucleic acid target. These techniques conventionally employ one or more oligonucleotide primers and a nucleic acid-polymerizing enzyme to synthesize copies of one or both strands of a nucleic acid template. Many different methods have been used for preparing biological samples in advance of the amplification procedure.

Multiplexed assays, which are capable of amplifying any of a plurality of different nucleic acid targets from a test sample in a single reaction, present special design challenges. For example, the targets amplifiable in a multiplex assay may be RNA targets, DNA targets, or even a combination of RNA and DNA targets. One challenge arises from the fact that RNA and DNA nucleic acids exhibit different chemical stabilities. Another challenge arises from a common desire to detect, with maximum sensitivity, any of a variety of related subtypes of a single target species. Even when subtype-specific primers are used in the reactions, it can be difficult to achieve substantially similar detection sensitivity for different subtypes of a single type of organism.

Accordingly, there is a need for a general technique which can enhance detectability of particular targets in nucleic acid amplification reactions. There is a further need for enhancing detectability of one or more targets in multiplex amplification reactions without substantially sacrificing detectability of other targets in the same reaction. The present invention addresses these needs.

Indeed, the invention disclosed herein provides a convenient method for preparing biological samples to be tested for the presence of nucleic acid targets using in vitro nucleic acid amplification. This method advantageously provides reliable results with a variety of nucleic acid-containing biological samples, while dramatically improving detectability of certain nucleic acid targets.

SUMMARY OF THE INVENTION

General speaking, the invention relates to a method of processing a biological sample. This method begins with a step for combining the biological sample with a pH buffer and a detergent to result in a first liquid composition having a first pH. It is convenient for the pH buffer and for the detergent to be in liquid form to simplify the combining step. Next, there is a step for mixing the first liquid composition with an alkaline composition to result in a second liquid composition having a second pH. Importantly, the second pH must be at least 0.2 pH units higher than the first pH, this being due to the added alkali. It is also important for the second pH to be lower than pH 9.5 to achieve good results. This is followed by a step for capturing one or more nucleic acids from the second liquid composition onto a solid support. Finally, there is a step for isolating the solid support having captured thereon any of the one or more nucleic acids. This may, for example, involve aspirating non-bound materials that remain in the liquid phase, thereby physically isolating the solid support and any nucleic acids captured thereon.

In one embodiment, the pH buffer and the detergent used in the combining step are each components of a buffered detergent solution, and the combining step involves combining the biological sample with an aliquot of the buffered detergent solution.

In another embodiment, the second pH, meaning the pH of the mixture that includes the biological sample, the buffer and the alkaline composition, is in the range of from pH 8.0 to pH 9.2. Preferably, when the second pH falls in the range of from pH 8.0 to 9.2, the capturing step involves capturing one or more RNA species or capturing one or more DNA species onto the solid support. In another preferred embodiment, when the second pH falls in the range of from pH 8.0 to 9.2, the first pH is in the range of from 6.5 to 8.0. In yet another preferred embodiment, when the second pH falls in the range of from pH 8.0 to 9.2, the capturing step can involve hybridizing one or more nucleic acids from the second liquid composition to one or more immobilized or immobilizable oligonucleotides complementary thereto. More preferably, the pH buffer and the detergent in the combining step are each components of a buffered detergent solution, and the combining step involves combining the biological sample with an aliquot of the buffered detergent solution. Still more preferably, the buffered detergent solution which includes the pH buffer and the detergent further includes the immobilized or immobilizable oligonucleotides that can be used for hybridizing and capturing nucleic acids from the second liquid composition that resulted from the mixing step.

In another preferred embodiment, the first pH, meaning the pH of the combination of the biological sample, the buffer and the detergent, is in the range of from 6.5 to 8.0. When this is the case, the capturing step preferably involves hybridizing the one or more nucleic acids to be captured to one or more immobilized or immobilizable oligonucleotides complementary thereto. More preferably, the pH buffer and the detergent used in the combining step are each components of a buffered detergent solution, and the combining step involves combining the biological sample with an aliquot of the buffered detergent solution. Still more preferably, the buffered detergent solution further includes the one or more immobilized or immobilizable oligonucleotides that are used for capturing nucleic acids from the second liquid composition. Yet still more preferably, the isolating step involves separating the solid support from material not captured thereon, and then washing the solid support having-captured thereon any nucleic acids. Even yet still more preferably, all of the above-described steps are carried out in a single reaction vessel.

In another preferred embodiment, the capturing step involves hybridizing the one or more nucleic acids that are to be captured to one or more immobilized or immobilizable oligonucleotides complementary thereto. When this is the case, it is preferred for the pH buffer and the detergent used in the combining step to each be components of a buffered detergent solution, and for the combining step to involve combining the biological sample with an aliquot of the buffered detergent solution. More preferably, this buffered detergent solution further includes the one or more immobilized or immobilizable oligonucleotides that can be used for capturing nucleic acids from the second liquid composition.

In another preferred embodiment, the detergent used in the combining step is an anionic detergent or a non-ionic detergent. When this is the case, the alkaline composition used in the mixing step preferably is a strong base, such as NaOH or LiOH.

In another embodiment, all of the steps for combining, mixing, capturing and isolating are carried out in a single reaction vessel. When this is the case, the mixing step preferably involves either agitating by orbital shaking or vortexing.

In another embodiment, the solid support in the capturing step includes a bead, such as a magnetic bead.

In another embodiment, the pKa of the pH buffer used in the combining step is between 6.0 and 9.0.

In another embodiment, at least one of the one or more nucleic acids captured in the capturing step is an RNA molecule.

In another embodiment, at least one of the one or more nucleic acids captured in the capturing step is a DNA molecule. In another preferred embodiment, the first pH falls in the range of from pH 6.5 to 8.0, and the second pH falls in the range of from pH 8.2 to 9.2. This relationship gave universally good results for processing both DNA templates and RNA templates. Thus, this combination of ranges is highly preferred for carrying out the invention.

Another general aspect of the invention relates to a method of processing a biological sample to obtain nucleic acids, and then using the obtained nucleic acids in a particular application. As above, this method begins with a step for combining the biological sample with a pH buffer and a detergent to result in a first liquid composition having a first pH. Next, there is a step for mixing with the first liquid composition an alkaline composition to result in a second liquid composition having a second pH. Again, it is important for the second pH to be at least 0.2 pH units higher than the first pH, and for the second pH to be lower than pH 9.5 to achieve good results. This is followed by a step for capturing one or more nucleic acids from the second liquid composition onto a solid support. Next, there is a step for isolating the solid support having captured thereon any of the one or more nucleic acids. This may, for example, involve aspirating non-bound materials that remain in the liquid phase, thereby physically isolating the solid support and any nucleic acids captured thereon. Finally, there is a step for performing an in vitro nucleic acid amplification reaction using as a template at least one of the nucleic acids captured on the solid support and isolated in the isolating step.

In a preferred embodiment, the second pH is in the range of from pH 8.0 to pH 9.2. When this is the case, it is preferred for the first pH to be in the range of from 6.5 to 8.0.

In another preferred embodiment, the first pH is in the range of from 6.5 to 8.0. When the first pH falls in the range of from 6.5 to 8.0, it is highly desirable for the second pH to fall in the range of from pH 8.2 to 9.2. Indeed, this set of ranges gave universally good results for processing both DNA templates and RNA templates. Thus, this combination of ranges is highly preferred for carrying out the invention.

In a different preferred embodiment, the in vitro nucleic acid amplification reaction is a multiplex reaction capable of amplifying more than one nucleic acid sequence. When this is the case, the one or more nucleic acids captured in the capturing step include two or more captured nucleic acids; the one or more nucleic acids isolated in the isolating step include two or more isolated nucleic acids; and the multiplex reaction uses as templates two of the of the captured and isolated nucleic acids. Indeed, it is highly preferred for the two nucleic acids used as templates in the multiplex reaction to include an RNA molecule and a DNA molecule.

In yet a different preferred embodiment, all of the steps for combining, mixing, capturing, isolating, and performing the nucleic acid amplification reaction are carried out in a single reaction vessel. When this is the case, it is preferred for the mixing step to involve either agitating by orbital shaking or vortexing.

DEFINITIONS

The following terms have the following meanings for the purpose of this disclosure, unless expressly stated to the contrary herein.

As used herein, "alkaline shock" refers to a transient high pH effected by first combining a biological sample with a pH buffer and a detergent to result in a first composition, and then mixing with that first composition an amount of an alkaline composition sufficient to increase the pH of the resulting mixture. Useful starting ranges for the pH of the first composition, and useful final ranges for the pH of the mixture subsequent to the addition of the alkaline composition are described herein.

As used herein, a "biological sample" is any tissue or polynucleotide-containing material obtained from a human, animal or environmental sample. Biological samples in accordance with the invention include peripheral blood, plasma, serum or other body fluid, bone marrow or other organ, biopsy tissues or other materials of biological origin. A biological sample may be treated to disrupt tissue or cell structure, thereby releasing intracellular components into a solution which may contain enzymes, buffers, salts, detergents and the like.

As used herein, "polynucleotide" means either RNA or DNA, along with any synthetic nucleotide analogs or other molecules that may be present in the sequence and that do not prevent hybridization of the polynucleotide with a second molecule having a complementary sequence.

As used herein, a "detectable label" is a chemical species that can be detected or can lead to a detectable response. Detectable labels in accordance with the invention can be linked to polynucleotide probes either directly or indirectly, and include radioisotopes, enzymes, haptens, chromophores such as dyes or particles that impart a detectable color (e.g., latex beads or metal particles), luminescent compounds (e.g., bioluminescent, phosphorescent or chemiluminescent moieties) and fluorescent compounds.

A "homogeneous detectable label" refers to a label that can be detected in a homogeneous fashion by determining whether the label is on a probe hybridized to a target sequence. That is, homogeneous detectable labels can be detected without physically removing hybridized from unhybridized forms of the label or labeled probe. Homogeneous detectable labels are preferred when using labeled probes for detecting amplified nucleic acids. Examples of homogeneous labels have been described in detail by Arnold et al., U.S. Pat. No. 5,283,174; Woodhead et al., U.S. Pat. No. 5,656,207; and Nelson et al., U.S. Pat. No. 5,658,737. Preferred labels for use in homogenous assays include chemiluminescent compounds (e.g., see Woodhead et al., U.S. Pat. No. 5,656,207; Nelson et al., U.S. Pat. No. 5,658,737; and Arnold, Jr., et al., U.S. Pat. No. 5,639,604). Preferred chemiluminescent labels are acridinium ester ("AE") compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, orthomethoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE).

A "homogeneous assay" refers to a detection procedure that does not require physical separation of hybridized probe from non-hybridized probe prior to determining the extent of specific probe hybridization. Exemplary homogeneous assays, such as those described herein, can employ molecular beacons or other self-reporting probes which emit fluorescent signals when hybridized to an appropriate target, chemiluminescent acridinium ester labels which can be selectively destroyed by chemical means unless present in a hybrid duplex, and other homogeneously detectable labels that will be familiar to those having an ordinary level of skill in the art.

As used herein, "nucleic acid amplification," or simply "amplification" refers to an in vitro procedure for obtaining multiple copies of a target nucleic acid sequence, its complement or fragments thereof.

By "target nucleic acid" or "target" is meant a nucleic acid containing a target nucleic acid sequence. In general, a target nucleic acid sequence that is to be amplified will be positioned between two oppositely disposed amplification oligonucleotides, and will include the portion of the target nucleic acid that is fully complementary to each of the amplification oligonucleotides.

By "target nucleic acid sequence" or "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto.

By "transcription associated amplification" is meant any type of nucleic acid amplification that uses an RNA polymerase to produce multiple RNA transcripts from a nucleic acid template. One example of a transcription associated amplification method, called "Transcription Mediated Amplification" (TMA), generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. The methods of Kacian et al. are preferred for conducting nucleic acid amplification procedures of the type disclosed herein.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spacial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present invention fall in a size range of about 10 to about 100 residues. Oligonucleotides may be purified from naturally occurring sources, but preferably are synthesized using any of a variety of well known enzymatic or chemical methods.

As used herein, a "probe" is an oligonucleotide that hybridizes specifically to a target sequence in a nucleic acid, preferably in an amplified nucleic acid, under conditions that promote hybridization, to form a detectable hybrid. A probe optionally may contain a detectable moiety which either may be attached to the end(s) of the probe or may be internal. The nucleotides of the probe which combine with the target polynucleotide need not be strictly contiguous, as may be the case with a detectable moiety internal to the sequence of the probe. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). The "target" of a probe generally refers to a sequence contained within an amplified nucleic acid sequence which hybridizes specifically to at least a portion of a probe oligonucleotide using standard hydrogen bonding (i.e., base pairing). A probe may comprise target-specific sequences and optionally other sequences that are non-complementary to the target sequence that is to be detected. These non-complementary sequences may comprise a promoter sequence, a restriction endonuclease recognition site, or sequences that contribute to three-dimensional conformation of the probe (e.g., as described in Lizardi et al., U.S. Pat. Nos. 5,118,801 and 5,312,728). Sequences that are "sufficiently complementary" allow stable hybridization of a probe oligonucleotide to a target sequence that is not completely complementary to the probe's target-specific sequence.

By "amplification oligonucleotide" is meant an oligonucleotide that is capable of participating in a nucleic acid amplification reaction to bring about the synthesis of multiple copies of a template nucleic acid sequence, or its complement. It is common for amplification reactions to employ at least two amplification oligonucleotides, with at least one of the amplification oligonucleotides serving as an amplification primer.

As used herein, an "amplification primer," or more simply "primer," is an oligonucleotide that hybridizes to a target nucleic acid, or its complement, and can be extended in a template-dependent primer extension reaction. For example, amplification primers may be optionally modified oligonucleotides which are capable of hybridizing to a template nucleic acid, and which have a 3' end that can be extended by a DNA polymerase activity. In general, a primer will have a downstream target-complementary sequence, and optionally an upstream sequence that is not complementary to target nucleic acids. The optional upstream sequence may, for example, serve as an RNA polymerase promoter or contain restriction endonuclease cleavage sites.

By "substantially homologous," "substantially corresponding" or "substantially corresponds" is meant that the subject oligonucleotide has a base sequence containing an at least 10 contiguous base region that is at least 70% homologous, preferably at least 80% homologous, more preferably at least 90% homologous, and most preferably 100% homologous to an at least 10 contiguous base region present in a reference base sequence (excluding RNA and DNA equivalents). Those skilled in the art will readily appreciate modifications that could be made to the hybridization assay conditions at various percentages of homology to permit hybridization of the oligonucleotide to the target sequence while preventing unacceptable levels of non-specific hybridization. The degree of similarity is determined by comparing the order of nucleobases making up the two sequences and does not take into consideration other structural differences which may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0-2 base differences.

By "substantially complementary" is meant that the subject oligonucleotide has a base sequence containing an at least 10 contiguous base region that is at least 70% complementary, preferably at least 80% complementary, more preferably at least 90% complementary, and most preferably 100% complementary to an at least 10 contiguous base region present in a target nucleic acid sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.) The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may range from 0-2 base mismatches.

By "sufficiently complementary" is meant a contiguous nucleic acid base sequence that is capable of hybridizing to another base sequence by hydrogen bonding between a series of complementary bases. Complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are preferably at least about 80%, more preferably at least about 90%, and most preferably about 100% complementary to a sequence to which an oligonucleotide is intended to specifically hybridize. Appropriate hybridization conditions are well known to those skilled in the art, can be predicted readily based on base sequence composition, or can be determined empirically by using routine testing (e.g., See Sambrook et al., *Molecular Cloning, A Laboratory Manual*, $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57 particularly at §§ 9.50-9.51, 11.12-11.13, 11.45-11.47 and 11.55-11.57).

By "capture oligonucleotide" is meant at least one nucleic acid oligonucleotide that provides means for specifically joining a target sequence and an immobilized oligonucleotide due to base pair hybridization. A capture oligonucleotide preferably includes two binding regions: a target sequence-binding region and an immobilized probe-binding region, usually contiguous on the same oligonucleotide, although the capture oligonucleotide may include a target sequence-binding region and an immobilized probe-binding region which are present on two different oligonucleotides joined together by one or more linkers. For example, an immobilized probe-binding region may be present on a first oligonucleotide, the target sequence-binding region may be present on a second oligonucleotide, and the two different oligonucleotides are joined by hydrogen bonding with a linker that is a third oligonucleotide containing sequences that hybridize specifically to the sequences of the first and second oligonucleotides.

By "immobilized oligonucleotide" or "immobilized nucleic acid," and variants thereof, is meant a nucleic acid that joins, directly or indirectly, a capture oligonucleotide to an immobilized support. An immobilized probe is an oligonucleotide joined to a solid support that facilitates separation of bound target sequence from unbound material in a sample. An "immobilizable" oligonucleotide is an oligonucleotide that can, by way of complementary base interactions with an oligonucleotide immobilized directly to a solid support, become immobilized to the solid support.

By "separating" or "purifying" is meant that one or more components of the biological sample are removed from one or more other components of the sample. Sample components include nucleic acids in a generally aqueous solution phase which may also include materials such as proteins, carbohydrates, lipids and labeled probes. Preferably, the separating or purifying step removes at least about 70%, more preferably at least about 90% and, even more preferably, at least about 95% of the other components present in the sample.

By "RNA and DNA equivalents" or "RNA and DNA equivalent bases" is meant molecules, such as RNA and DNA, having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "consisting essentially of" is meant that additional component(s), composition(s) or method step(s) that do not materially change the basic and novel characteristics of the present invention may be included in the compositions or kits or methods of the present invention. Such characteristics include the ability to selectively detect target nucleic acids in biological samples such as whole blood or plasma. Any component(s), composition(s), or method step(s) that have a material effect on the basic and novel characteristics of the present invention would fall outside of this term.

BRIEF DESCRIPTION OF THE DRAWINGS

FIG. 2A presents results measured as % Positivity as a function of the concentration of NaOH used in the alkaline shock step. FIG. 2B presents results measured as % CV (coefficient of variability) as a function of the concentration of NaOH used in the alkaline shock step. FIG. 2C presents results measured as the Mean RLU as a function of the concentration of NaOH used in the alkaline shock step.

FIG. 3A shows results for HBV subtype-B. FIG. 3B shows results for HBV subtype-C. FIG. 3C shows results for HBV subtype-A. Control trials are indicated by open bars. Results from trials receiving an alkaline shock are indicated by filled bars.

FIG. 4A shows results for HCV-1a virus. FIG. 4B shows results for HCV-2b virus. FIG. 4C shows results for HIV-1b virus. Control trials are indicated by open bars. Results from trials receiving an alkaline shock are indicated by filled bars.

DETAILED DESCRIPTION OF THE INVENTION

Figure 1:
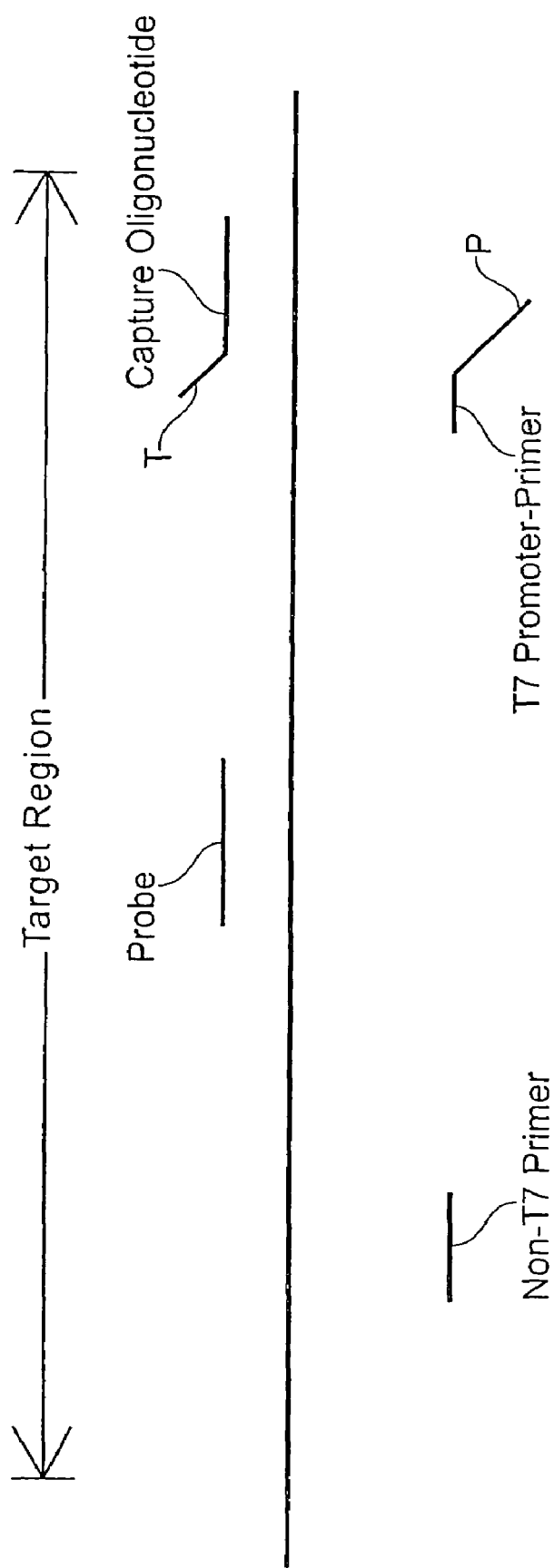
FIG. 1 is a schematic diagram illustrating the various polynucleotides that can be used for detecting a target region within a model target nucleic acid (represented by a thick horizontal line). Positions of the following nucleic acids are shown relative to the target region: "Capture Oligonucleotide" refers to the nucleic acid used to hybridize to and capture the target nucleic acid prior to amplification, where "T" refers to a tail sequence used to hybridize an immobilized oligonucleotide having a complementary sequence (not shown); "Non-T7 Primer" and "T7 Promoter-Primer" represent two amplification primers used for conducting TMA, where "P" indicates the promoter sequence of the T7 promoter-primer; and "Probe" refers to the probe used for detecting amplified nucleic acid.

Herein there is disclosed a method of preparing a nucleic acid-containing biological sample. The method can be used to prepare both DNA and RNA templates from viral, bacterial or eucaryotic sources, and can be used for enhancing the sensitivity of amplification reactions conducted using the prepared nucleic acids as templates. Surprisingly, all of these advantages can be achieved without redesigning any of the oligonucleotides used in the target-capture, amplification, or detection steps of a nucleic acid detection procedure.

Generally speaking, subject matter of the invention relates to the unexpected discovery that addition of an alkaline solution to a buffered detergent solution which contains a biological sample, such that the pH after mixing falls within a specified range, provides certain advantages when the processed sample subsequently serves as a source of templates in a nucleic acid amplification reaction. Preferably, the invented sample processing procedure involves a target-capture component wherein conditions following addition of the alkali are compatible with the formation of polynucleotide hybrids that include an immobilized capture oligonucleotide and a polynucleotide liberated from the biological sample. As indicated by the evidence presented below, advantages of the invention are not achieved when the alkali and pH buffered detergent solutions are first combined, and then added to the biological sample.

An observation which prompted development of the invention related to the differential ability of an amplified assay to detect different HBV subtypes. More specifically, a multiplexed assay capable of amplifying and detecting any of HIV-1, HCV and HBV nucleic acid targets was found to exhibit widely different sensitivities for different HBV subtypes. As indicated below, the assay yielded approximately equivalent sensitivities for subtypes-A and -C, but a sensitivity for subtype-B that was nearly 16 fold reduced. This was despite the fact that the three subtypes of HBV share a close phylogenetic relationship, and despite the fact that a common set of primers and probes can be used in the assay procedure. Because it was desirable to detect all of the different subtypes with great sensitivity, it was of interest to enhance assay sensitivity for detection of one viral subtype without substantially compromising detection of the other subtypes.

Improving the sensitivity of HBV subtype-B detection conceivably could have been accomplished by any of several approaches. For example, redesigning the oligonucleotide components used in the assay may have led to improvements. However, even if this could have been accomplished, the solution would only have been specific for the redesigned assay. A more desirable solution would provide a general means for improving HBV subtype-B detectability, and perhaps the performance of other assays as well. Thus, one object of the invention related to a method of improving the detectability of at least one target in a multiplexed assay.

Preferred Buffers and pH Ranges

Buffers useful for carrying out the invented alkaline shock-based sample preparation method preferably have pKa values in the range of from about 6.0 to about 9.0. An exemplary buffer used for demonstrating utility of the invention is HEPES (N-2-Hydroxyethylpiperazine-N'-2-Ethane Sulfonic Acid), which has a pKa of 7.55 at 20° C., and which has its strongest buffer capacity in the pH range of from 6.8 to 8.2. Of course, success of the technique is not limited by the use of any particular buffer.

According to a preferred method for carrying out the invention, a biological sample is first combined with a pH buffer and a detergent to give a first composition, which is then combined with an aliquot of a concentrated hydroxide solution to effect the alkaline shock. The buffer and detergent conveniently can be combined with each other so that a single aliquot of a buffered detergent solution can be dispensed in a reagent addition step. It is preferred for the buffered detergent solution to additionally contain one or more optional immobilizable or immobilized capture oligonucleotides to further reduce the complexity of the reagent addition steps, thereby particularly adapting the method to automation by the use of robotic pipettors. When the alkaline shock sample preparation method is performed by combining an aliquot of a liquid, or liquified biological sample with a single reagent composition that contains the buffer, the detergent, and the capture oligonucleotide and a solid support (i.e., a bead) to effect the capture, the reagent composition is termed, "lysis/capture reagent." Excellent results have been achieved using lysis/capture reagents having buffer concentrations in the range of from about 200 mM to about 800 mM, which produced final buffer concentrations after combining lysis/capture reagent with the biological sample in the range of from about 90 mM to about 355 mM. Of course, changes to the buffer strength require that the amount of added alkaline hydroxide be adjusted to bring the final pH of the mixture into one of the ranges specified herein. Thus, success of the technique is not limited by the amounts or concentrations of the buffer in the mixture prior to addition of the alkaline solution which effects alkaline shock.

Preferably the starting pH range for the combination of a buffered detergent solution mixed with a biological sample before addition of alkali to effect that alkaline shock is in the range of from pH 6.5 to 8.0, still more preferably in the range of from pH 7.0 to 8.0, or yet still more preferably in the range of from pH 7.0 to 7.5. Testing conducted using buffered detergent solutions having starting a starting pH of 7.0, 7.5 and 8.0 all led to good results when preparing nucleic acid templates according to the alkaline shock protocol, and then amplifying and detecting those templates. These results supported useful ranges for the starting pH of a first composition that included the biological sample undergoing specimen processing, the pH buffer, and the detergent prior to addition of the alkaline composition. Notably, because this testing was performed using a co-amplifiable RNA internal control, and because all tests yielded valid results, it was concluded that RNA was stable over this range of starting pH conditions. To simplify the description of the invention, the Examples presented below all employed a biological sample/buffer/detergent combination having a starting pH of about 7.5 prior to addition of an alkaline hydroxide. Again, success of the alkaline shock sample processing technique can be achieved over a wide starting pH range.

Treatment Methods—Alkaline and Detergent Conditions

In a preferred embodiment of the invented method, a first composition that includes a biological sample, a pH buffer and a detergent, is combined with a second composition that includes an alkaline composition. The combination is mixed and preferably allowed to incubate with an immobilized capture probe, and perhaps also a soluble capture probe capable of forming a bridge between an immobilized probe and a target nucleic acid of interest. As the method is typically practiced, alkaline hydroxide is added to a tube or other reaction vessel that already contains the first composition. In a highly preferred embodiment, the first composition either also includes, or is combined with the soluble capture probe and immobilized capture probe prior to addition of the alkali hydroxide.

Substances which may be used as the alkaline composition to effect the alkaline shock may be any solid, liquid or gaseous agent which creates a strong alkaline solution when dissolved in aqueous solution. Strong bases are highly preferred alkaline compositions (hereafter referred to generally as "alkaline hydroxides") useful in connection with the invention. Examples of preferred alkaline hydroxides that can be used to carry out the invented sample preparation method include sodium hydroxide, lithium hydroxide, potassium hydroxide, and the like. Although it is contemplated that solid alkaline compositions can be combined with the first composition that includes the buffered detergent and biological sample solution (as might be achieved by adding the first composition to a tube already containing a measured amount of the dry alkaline hydroxide reagent), it is preferred to use alkaline compositions in solution form.

To achieve the benefits of the invention, the amount of alkaline composition added to the composition that includes the biological sample, the pH buffer and detergent is critical, and can easily be gauged by the final pH of the complete mixture. It is preferred that the amount of added alkaline hydroxide is sufficient to increase the pH of the resulting mixture by at least 0.2 pH units, but not so much as to raise the pH above 9.5, more preferably not above 9.2, more preferably not above 9.0, still more preferably not above 8.8. Testing results confirm that useful amounts of added alkaline hydroxide are those amounts that cause the final pH of the mixture to fall within a specified range. The preferred final pH range is from between pH 8.0 and 9.2, more preferably from between pH 8.2 and 9.2, and still more preferably from between pH 8.2 and 8.8. As reiterated below, uniformly good results were achieved when the final pH of the mixture following the alkaline shock fell in the range of from pH 8.2 to 9.2. This was true for both DNA and RNA templates. When the amount of added alkaline hydroxide caused the mixture to exceed a final pH of 9.5, poor results were achieved.

Preferred Detergents

Detergents that can be used in connection with the invention may be anionic detergents, non-ionic detergents, zwitterionic detergents, or cationic detergents. Of these, the anionic and non-ionic detergents are the most preferred. The detergent concentration in the lysis/capture reagent is preferably between 0.01 and 15 wt. %, the particularly preferred concentration ranging between 0.05 to 10 wt. %. Based on the demonstrated use of 400 µl of lysis/capture reagent and 500 µl of biological sample, the final concentration of detergent in the mixed composition that includes buffer, detergent and biological sample, preferably falls in the range of from about 0.01 wt. % to about 6.7 wt. %. Strong anionic detergents, including sulfates of alkyl alcohols and N-acyl-amino acids are highly preferred. While the precise nature of the detergent used for conducting the alkaline shock-based sample preparation procedure is not believed critical, examples of particularly preferred detergents include lithium lauryl sulfate (LLS), and sodium dodecyl sulfate (SDS).

Treatment Period

In a preferred embodiment, an aliquot of an alkaline hydroxide solution is combined in a reaction vessel with a composition that includes a biological sample, a buffer, a detergent, and, if sequence-specific target-capture is to be performed, one or more immobilizable capture oligonucleotides. After a period of from about one second to about one hour, the contents are agitated to ensure uniform mixing, and the target-capture process which involves the immobilization, whether direct or indirect, of a polynucleotide liberated from the biological sample, and an immobilized oligonucleotide follows. Of course, non-specific target capture also can be employed. To facilitate laboratory productivity, the length of time during which the target-capture step is performed is desirably no longer than necessary. However, because nucleic acids liberated from the biological sample will be stable in the mixed composition subsequent to addition of the alkaline hydroxide, allowing the mixtures to stand for up to at least a few hours is not believed harmful to the target nucleic acids. Thus, the treatment conditions associated with the alkaline shock are believed quite mild.

Plastic Containers Disposed in an Automated Analyzer

The invented method of sample preparation preferably is carried out in a disposable reaction vessel, such as a plastic tube, or a disposable unit comprising a plurality of tubes held in a spaced-apart configuration. For example, the disposable reaction vessel is preferably positioned within an analytical device at the time that the alkaline hydroxide solution is added, and the addition step is preferably carried out by a manual, or an automated or robotic pipetting device. In a highly preferred embodiment, the disposable reaction vessel is loaded into the analytical device, and a manual, or an automated or robotic pipetting device adds to the vessel an aliquot of the biological sample and an aliquot of lysis/capture reagent which includes a pH buffer and a detergent for lysing or disrupting biological membranes, such as cell membranes, viral envelopes, and the like. The lysis/capture reagent preferably also contains an immobilizable capture oligonucleotide and insoluble beads for capturing polynucleotides liberated from the biological sample. Thereafter, the same or a different automated or robotic pipetting device adds to the tube an aliquot of alkaline hydroxide solution. The contents of the tube can then be agitated to ensure complete mixing, and the mixed sample incubated at a temperature and for a period sufficient to permit capture of the liberated polynucleotides. Because the alkaline shock conditions are mild, there is no substantial chemical degradation that is known to occur by extended or variable periods of standing, as may occur when different analytical protocols are executed on the automated analyzer in a single daily cycle of laboratory testing.

Target Capture—Methods and Oligonucleotides

The disclosed alkaline shock-based sample preparation method has been demonstrated to have particular value when coupled with a target capture procedure that enriches the sample for nucleic acids. Separate preferred embodiments rely on non-specific target capture (i.e., where nucleic acids are captured in a manner substantially independent of the base sequence of the nucleic acids), and on sequence-specific target capture. Either or both of these methods can employ an immobilizable or immobilized capture oligonucleotide.

Preferred capture oligonucleotides include a first sequence that is complementary to a polynucleotide containing a target sequence which is to be amplified, covalently attached to a second sequence (i.e., a "tail" sequence) that serves as a target for immobilization on a solid support. Any backbone to link the base sequence of a capture oligonucleotide may be used. In certain preferred embodiments the capture oligonucleotide includes at least one methoxy linkage in the backbone. The tail sequence, which is preferably at the 3' end of a capture oligonucleotide, is used to hybridize to a complementary base sequence to provide a means for capturing the hybridized target nucleic acid in preference to other components in the biological sample.

Although any base sequence that hybridizes to a complementary base sequence may be used in the tail sequence, it is preferred that the hybridizing sequence span a length of about 5-50 nucleotide residues. Particularly preferred tail sequences are substantially homopolymeric, containing about 10 to about 40 nucleotide residues, or more preferably about 14 to about 30 residues. A capture oligonucleotide according to the present invention may include a first sequence that specifically binds a target polynucleotide, and a second sequence that specifically binds an oligo(dT) stretch immobilized to a solid support.

Using the components illustrated in FIG. 1, one assay for detecting nucleic acid sequences in a biological sample includes the steps of capturing the target nucleic acid using the capture oligonucleotide, amplifying the captured target region using at least two amplification oligonucleotides, or at least two primers, and detecting the amplified nucleic acid by first hybridizing the labeled probe to a sequence contained in the amplified nucleic acid and then detecting a signal resulting from the bound labeled probe.

The capturing step preferably uses a capture oligonucleotide where, under hybridizing conditions, one portion of the capture oligonucleotide specifically hybridizes to a sequence in the target nucleic acid and a tail portion serves as one component of a binding pair, such as a ligand (e.g., a biotin-avidin binding pair) that allows the target region to be separated from other components of the sample. Preferably, the tail portion of the capture oligonucleotide is a sequence that hybridizes to a complementary sequence immobilized to a solid support particle. Preferably, first, the capture oligonucleotide and the target nucleic acid are in solution to take advantage of solution phase hybridization kinetics. Hybridization produces a capture oligonucleotide:target nucleic acid complex which can bind an immobilized probe through hybridization of the tail portion of the capture oligonucleotide with a complementary immobilized sequence. Thus, a complex comprising a target nucleic acid, capture oligonucleotide and immobilized probe is formed under hybridization conditions. Preferably, the immobilized probe is a repetitious sequence, and more preferably a homopolymeric sequence (e.g., poly-A, poly-T, poly-C or poly-G), which is complementary to the tail sequence and attached to a solid support. For example, if the tail portion of the capture oligonucleotide contains a poly-A sequence, then the immobilized probe would contain a poly-T sequence, although any combination of complementary sequences may be used. The capture oligonucleotide may also contain "spacer" residues, which are one or more bases located between the base sequence that hybridizes to the target and the base sequence of the tail that hybridizes to the immobilized probe. Any solid support may be used for binding the target nucleic acid:capture oligonucleotide complex. Useful supports may be either matrices or particles free in solution (e.g., nitrocellulose, nylon, glass, polyacrylate, mixed polymers, polystyrene, silane polypropylene and, preferably, magnetically attractable particles). Methods of attaching an immobilized probe to the solid support are well known. The support is preferably a particle which can be retrieved from solution using standard methods (e.g., centrifugation, magnetic attraction of magnetic particles, and the like). Preferred supports are paramagnetic monodisperse particles (i.e., uniform in size ± about 5%).

Retrieving the target nucleic acid:capture oligonucleotide:immobilized probe complex effectively concentrates the target nucleic acid (relative to its concentration in the biological sample) and purifies the target nucleic acid from amplification inhibitors which may be present in the biological sample. The captured target nucleic acid may be washed one or more times, further purifying the target, for example, by resuspending the particles with the attached target nucleic acid:capture oligonucleotide:immobilized probe complex in a washing solution and then retrieving the particles with the attached complex from the washing solution as described above. In a preferred embodiment, the capturing step takes place by sequentially hybridizing the capture oligonucleotide with the target nucleic acid and then adjusting the hybridization conditions to allow hybridization of the tail portion of the capture oligonucleotide with an immobilized complementary sequence (e.g., as described in PCT No. WO 98/50583). After the capturing step and any optional washing steps have been completed, the target nucleic acid can then be amplified. To limit the number of handling steps, the target nucleic acid optionally can be amplified without releasing it from the capture oligonucleotide.

Useful capture oligonucleotides may contain mismatches to the above-indicated sequences, as long as the mismatched sequences hybridize to the nucleic acid containing the sequence that is to be amplified.

Useful Amplification Methods

Amplification methods useful in connection with the present invention include: Transcription Mediated Amplification (TMA), Nucleic Acid Sequence-Based Amplification (NASBA), the Polymerase Chain Reaction (PCR), Strand Displacement Amplification (SDA), and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, published European patent application EP 0 525 882, U.S. Pat. Nos. 4,965,188, 5,455,166, 5,472,840 and Lizardi et al., *BioTechnology* 6:1197 (1988). The disclosures of these documents which describe how to perform nucleic acid amplification reactions are hereby incorporated by reference.

In a preferred embodiment of the invention, target nucleic acid sequences are amplified using a TMA protocol. According to this protocol, the reverse transcriptase which provides the DNA polymerase activity also possesses an endogenous RNase H activity. One of the primers used in this procedure contains a promoter sequence positioned upstream of a sequence that is complementary to one strand of a target nucleic acid that is to be amplified. In the first step of the amplification, a promoter-primer hybridizes to the target RNA at a defined site. Reverse transcriptase creates a complementary DNA copy of the target RNA by extension from the 3' end of the promoter-primer. Following interaction of an opposite strand primer with the newly synthesized DNA strand, a second strand of DNA is synthesized from the end of the primer by reverse transcriptase, thereby creating a double-stranded DNA molecule. RNA polymerase recognizes the promoter sequence in this double-stranded DNA template and initiates transcription. Each of the newly synthesized RNA amplicons re-enters the TMA process and serves as a template for a new round of replication, thereby leading to an exponential expansion of the RNA amplicon. Since each of the DNA templates can make 100-1000 copies of RNA amplicon, this expansion can result in the production of 10 billion amplicons in less than one hour. The entire process is autocatalytic and is performed at a constant temperature.

Kits

The invention also embraces kits that can be used for carrying out alkaline shock-based sample preparation procedures. Kits in accordance with the invention will include in separate vials or containers: a lysis/capture reagent and an alkaline hydroxide. In certain embodiments of the invention, one or both of these reagents is a dry, lyophilized, or semi-solid composition which can be reconstituted with a liquid component, such as water, prior to use. In certain highly preferred embodiments, the alkaline hydroxide composition requires reconstitution with a liquid agent prior to use. In other embodiments, the alkaline hydroxide is packaged in the kit as a liquid composition. The lysis/capture reagent preferably includes a detergent and a buffer with a pH less than 8.0 upon reconstitution, if reconstitution is necessary.

Preferred Embodiments of the Invention

To ensure development of a general procedure for enhancing detectability of DNA targets without substantially compromising detectability of RNA targets in nucleic acid amplification-based assays, certain aspects of the invention were created using a model multiplex assay essentially as described in Example 7 of published International Patent Application No. PCT/US03/18993, the disclosure of which is incorporated by reference. This assay, which is capable of amplifying both RNA targets (HIV-1 and HCV) and a DNA target (HBV), employs a common set of primers for amplifying all of HBV subtypes A-C. Accordingly, the procedures described below essentially isolated sample preparation as a variable.

The model assay used in the procedures described herein involved three main steps which all took place in a single tube: sample preparation; HIV-1 or HCV RNA or HBV DNA target amplification; and detection of the amplification products (amplicon) by the Hybridization Protection Assay (HPA). During sample preparation, viral RNA and DNA were isolated from plasma specimens via the use of target capture. Plasma was combined with a buffered detergent solution to facilitate solubilization of the viral envelope, denaturation of proteins and release viral genomic RNA and/or DNA from viral particles contained in the specimen. An alkaline shock effected by the further addition of an alkaline hydroxide solution served as a test step during development of the invention. For simplicity, the buffered detergent solution that was combined with the plasma specimen was termed, "lysis/capture reagent." Oligonucleotides (capture oligonucleotides) that were homologous to conserved regions of HIV-1, HCV, and HBV were hybridized to the HIV-1 or HCV RNA or HBV DNA targets, if present, in the test specimen. Hybridized targets were then captured onto magnetic microparticles, and separated from the bulk plasma in a magnetic field. Wash steps were used to remove extraneous plasma components from the reaction tube. Next, any captured viral nucleic acids were used as templates in a primer-dependent in vitro nucleic acid amplification reaction. Target amplification in the model assay occurred via TMA, a transcription-based nucleic acid amplification method that uses two enzymes, MMLV reverse transcriptase and T7 RNA polymerase. The model assay was capable of amplifying regions of HIV-1 RNA, HCV RNA, and/or HBV DNA. Detection of amplicons was achieved by HPA using a mixture of single-stranded nucleic acid probes that were complementary to the amplicons. Each nucleic acid probe harbored a chemiluminescent label, and hybridized specifically to one of the amplicons. A "selection" reagent differentiated between hybridized and unhybridized probes by inactivating the label on unhybridized probes. During the detection step, the chemiluminescent signal produced by the hybridized probe was measured in a luminometer and was reported as relative light units (RLU).

The integrity of assay results was verified by the use of an Internal Control (IC) that was added to each test specimen, external control, or assay calibrator tube via the working lysis/capture reagent. The IC in this reagent controlled for specimen processing, amplification, and detection steps. The IC signal in each tube or assay reaction was discriminated from the HIV-1/HCV/HBV signal by the differential kinetics of light emission from probes with different labels. The IC amplicon was detected using a probe with rapid emission of light (termed flasher signal). Amplicon specific for HIV-1/HCV/HBV was detected using probes with relatively slower kinetics of light emission (termed glower signal). Those having an ordinary level of skill in the art will appreciate that the Dual Kinetic Assay (DKA) is a standard method used to differentiate between the signals from flasher and glower labels. When used for simultaneous detection of HIV-1, HCV, and HBV, the model assay differentiated between IC and combined HIV-1/HCV/HBV signals, but did not discriminate between individual HIV-1, HCV, and HBV signals.

The interpretation of assay results relied on signals representing detection of one of the target nucleic acids as well as the IC. More specifically, two cutoffs were determined for each assay: one for the Analyte signal (glower signal), termed the Analyte Cutoff, and one for the IC signal (flasher signal), termed the IC Cutoff. For each sample, an Analyte signal RLU value and IC signal RLU value were determined. Analyte signal RLU divided by the Analyte Cutoff was termed the Analyte Signal/Cutoff, or "S/CO." For a sample with Analyte signal less than the Analyte Cutoff (i.e., Analyte S/CO<1.00), the Internal Control (IC) signal must be greater than or equal to the Internal Control Cutoff (IC Cutoff) for the result to be valid. In this case the Internal Control result will be considered to be valid, and the sample will be reported as nonreactive. For a sample with the Analyte signal less than the Analyte Cutoff (i.e., Analyte S/CO<1.00) and the Internal Control signal less than the Internal Control Cutoff, the Internal Control result will be considered as invalid, and the sample result will be invalid. For all samples, the Internal Control signal may not exceed 475,000 RLU. In such an instance, the sample will automatically be reported as invalid.

As indicated above, the amplification technique used to illustrate the invention was the Transcription Mediated Amplification. However, the disclosed sample preparation method can be used in conjunction with any in vitro nucleic acid amplification technique that will be familiar to those having an ordinary level of skill in the art. This is because the invented method operates to improve the lysis and target-capture steps which are independent of the nucleic acid amplification procedure.

The following Example describes preliminary experiments that empirically established the amount of an alkaline hydroxide solution that could be added to a sample of lysis/capture reagent without completely exceeding the buffer capacity of the mixture. In this instance, the exemplary buffered detergent solution was a HEPES-buffered lithium lauryl sulfate solution that included capture oligonucleotides and magnetic beads. These procedures were used to establish a pH profile only, and did not involve nucleic acid amplification. The HEPES (N-2-hydroxyethylpiperazine-N'-2-ethanesulfonic acid) component of the lysis/capture reagent has a pKa of about 7.5, and conventionally is used for buffering solutions in the range of from pH 6.8 to 8.2. Buffers other than HEPES can be used to carry out the invented sample preparation procedure, provided that the added alkali solution is added in an amount such that the final pH falls within the range specified below. Of course, it is preferred for the starting pH of the buffered detergent solution to be approximately neutral to slightly alkaline, meaning in the range of from about pH 6.5 to about 8.0, or more preferably from about pH 7.0 to about 8.0, or still more preferably from about pH 7.0 to about 7.5.

Example 1 describes the effect of adding an alkaline hydroxide solution to a HEPES-buffered detergent solution that either included, or did not include an added plasma sample. The results from this procedure provided an empirical basis for determining the final pH of mixtures created using different amounts of the hydroxide solution.

EXAMPLE 1

Determining the pH Effect of Adding Alkali to a Buffered Detergent Solution which Includes a Plasma Sample Aliquots (400 µl) of a lysis/capture reagent (i.e., a buffered detergent solution) were dispensed into plastic reaction tubes. The lysis/capture reagent contained soluble capture oligonucleotides and about 40 µg of 0.7-1.05 µ paramagnetic particles (Seradyn, Indianapolis, Ind.) covalently linked to poly-(dT$_{14}$). Capture oligonucleotides were capable of simultaneously hybridizing to the particle-bound poly-(dT) and to the nucleic acids of HBV subtypes-A, -B or -C. The lysis/capture reagent further included an HIV-1 internal amplification control template, HIV-1 and HCV-specific capture oligonucleotides, about 800 mM HEPES (pH 7.5), and about 10% wt/vol lithium lauryl sulfate. Half of the reaction tubes also received an aliquot (500 µl) of a processed control plasma that did not contain fibrin. The tubes then received 100 µl aliquots of NaOH solution having a concentration in the range of from 1.0 to 2.5N. One set of tubes containing lysis/capture reagent, or the combination of lysis/capture reagent and plasma sample were reserved as controls that did not receive an aliquot of NaOH solution. All samples were mixed using a mechanical vortexer, and the pH values of the resulting mixtures were determined using a Model 9100 pH meter from VWR Scientific Products (Chester, Pa.). Results from these procedures are presented in Table 1.

TABLE 1

Titration of Alkali into a Buffered Detergent Solution Combined with a Plasma Sample

| | pH After Mixing | |
|---|---|---|
| Conc. of added NaOH | Sample: Lysis/Capture Reagent | Sample: Lysis/Capture Reagent + Plasma |
| None | 7.45 | 7.45 |
| 1.0 N | 8.05 | 8.05 |
| 1.4 N | 8.31 | 8.35 |
| 1.8 N | 8.65 | 8.76 |
| 2.2 N | 9.85 | 10.62 |
| 2.5 N | 13.2 | 12.6 |

The results presented in Table 1 indicated that addition of 100 µl of an NaOH solution having a concentration of 2.2N or greater started to exceed the buffer capacity of the buffered detergent solution, with or without an added plasma sample. This was based on the observation that the final pH of the mixtures increased greater than one pH unit only when concentrations of NaOH at 2.2N and higher were used. These results provided a basis for additional studies aimed at quantifying the effect of added alkali on the ability to detect DNA targets in in vitro amplification reactions, and provided guidance useful for adapting the procedure to the use of RNA targets which might be subject to hydrolysis under conditions of elevated pH.

The following Example describes how varying amounts of added alkali influenced detection of HBV subtype-B in an in vitro amplification system that involved viral lysis, capture of released nucleic acids, amplification and detection steps. In this procedure, the monitored assay parameters included % positivity for detection, % CV (coefficient of variability), and the mean quantitative signal strength (measured in relative light units, or "RLU"). Those having an ordinary level of skill in the art will appreciate that low % CV values advantageously indicate higher levels of assay precision, and so are greatly preferred.

Example 2 describes procedures that defined useful amounts of alkali that could be added to a mixture of virus-containing plasma and a lysis/capture reagent preliminary to conducting an in vitro nucleic acid amplification reaction.

EXAMPLE 2

Sample Preparation that Includes Alkaline Shock Improves Assay Performance

Figure 2A:
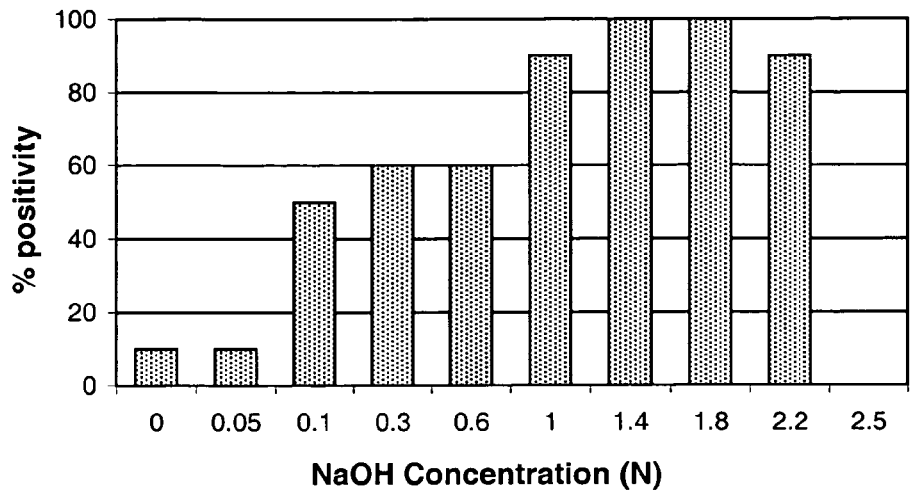
FIGS. 2A-2C are a series of bar graphs displaying results from trials conducted using different concentrations of NaOH solution.
Figure 2B:
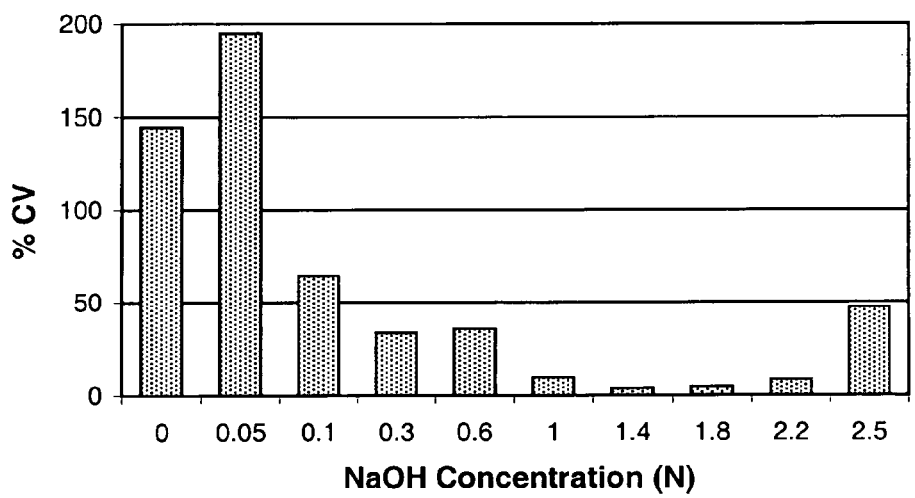
Figure 2C:
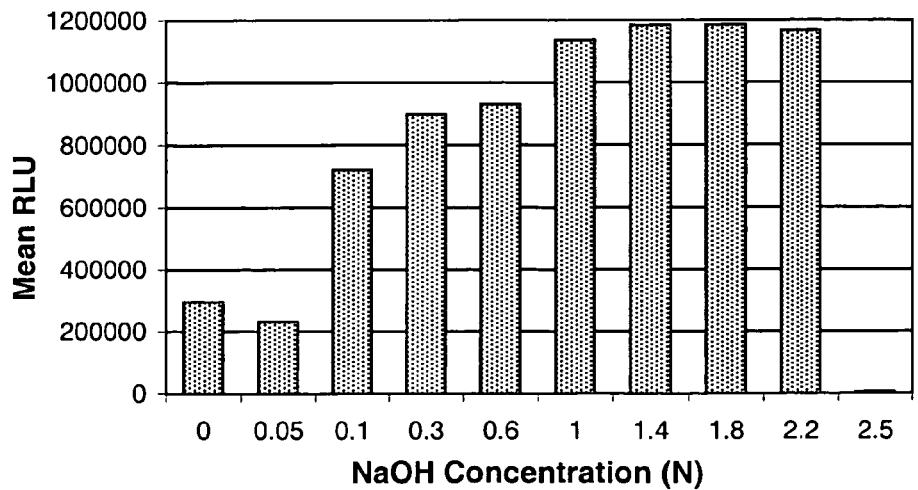

A 400 µl aliquot of the lysis/capture reagent described in Example 1 was combined in a plastic reaction tube with 500 µl of a plasma sample obtained from an individual infected with HBV subtype-B. Control tubes included virus-negative plasma instead of virus-positive samples. All plasma samples used as the source of viral templates in this procedure had been diluted 1:3 with virus-negative processed control plasma. Next, 100 µl aliquots of NaOH solutions having different concentrations were added to the different tubes containing the combination of the lysis/capture reagent and plasma. The alkaline solutions used in the procedure had NaOH concentrations ranging from 0.05 to 2.5N. A control tube included water in place of the NaOH solution. The mixtures were vortexed briefly to ensure mixing, heated to 60° C. for about 20 minutes, and then cooled to room temperature for 15 minutes to allow hybridization and target capture. A magnetic field was applied to collect the particle complexes containing the immobilized capture oligonucleotide and HBV DNA using procedures such as those described by Wang in U.S. Pat. No. 4,895,650. The particles were then washed twice with 1 ml of a washing buffer (10 mM HEPES at pH 7.5, 6.5 mM NaOH, 1 mM EDTA, 0.3% (v/v) ethanol, 0.02% (w/v) methyl-paraben, 0.01% (w/v) propyl-paraben, 150 mM NaCl, 0.1% (w/v) sodium lauryl sulfate). Washed particles were resuspended in 75 µl of an amplification reagent, and the contents of the tube overlaid with inert oil to prevent evaporation. The amplification reagent included salts, nucleotides, ribonucleotides, HBV-specific primers, as well as primers capable of amplifying HIV-1 and HCV target sequences. After vortexing briefly, the mixture was first incubated at 60° C. for 10 minutes to facilitate primer annealing, and then equilibrated at 41.5° C. for 10 minutes. Aliquots of pre-warmed enzyme reagent that included Moloney Murine Leukemia Virus (MMLV) reverse transcriptase (5,600 units/reaction) and T7 RNA polymerase (3,500 units/reaction) were then added to the mixtures. After a one hour incubation at 41.5° C., the reaction was complete and HBV amplification products were detected using an acridinium ester-labeled hybridization probe in a homogenous protection assay, essentially as described under Example 1 of published International Patent Application No. PCT/US03/18993. Reactions that gave positive signals when hybridized with a probe specific for the internal control amplicon, or with a probe specific for the HBV amplicon, were scored as valid runs. In order for a valid run to be considered positive for the presence of HBV amplicons, the chemiluminescent signal indicating probe hybridization must have exceeded 50,000 RLU in an assay. Results from these procedures are presented in Table 2, and in FIGS. 2A-2C.

TABLE 2

Optimizing Conditions for Alkaline Shock

| Additive | Plasma Sample | % Positive | CV % | Mean RLU |
|---|---|---|---|---|
| Water | control | 0 | 37 | 2231 |
| (control) | HBV-B 1:3 | 10 | 144 | 296066 |
| 0.05 N NaOH | control | 0 | 23 | 2709 |
| | HBV-B 1:3 | 10 | 195 | 232295 |
| 0.1 N NaOH | control | 0 | 33 | 2248 |
| | HBV-B 1:3 | 50 | 64 | 721476 |
| 0.3 N NaOH | control | 0 | 20 | 3546 |
| | HBV-B 1:3 | 60 | 34 | 898200 |
| 0.6 N NaOH | control | 0 | 37 | 4023 |
| | HBV-B 1:3 | 60 | 36 | 930407 |
| 1.0 N NaOH | control | 0 | 17 | 5017 |
| | HBV-B 1:3 | 90 | 10 | 1136773 |
| 1.4 N NaOH | control | 0 | 42 | 4387 |
| | HBV-B 1:3 | 100 | 4 | 1183610 |
| 1.8 N NaOH | control | 0 | 24 | 4216 |
| | HBV-B 1:3 | 100 | 5 | 1184132 |
| 2.2 N NaOH | control | 0 | 16 | 4559 |
| | HBV-B 1:3 | 90 | 8 | 1166869 |
| 2.5 N NaOH | control | 0 | 211 | 13087 |
| | HBV-B 1:3 | 0 | 47 | 5931 |

The results from these procedures indicated that sample preparation which included an alkaline shock step advantageously led to dramatically improved assay performance. Notably, the fact that all of the assays differed only by the nature of the alkaline shock step confirmed that the benefits achievable by the use of an alkaline shock did not depend on the particular oligonucleotides used in the procedure. Indeed, the control trial that received an aliquot of water instead of NaOH solution gave relatively low % positivity levels and undesirably high % CV values. Conversely, an alkaline shock performed using an NaOH solution having a concentration in the range of from 0.1 to 2.2N gave dramatically greater % positivity levels with increased precision, as judged by the reduced % CV values.

Importantly, these results also provided evidence for an optimal range of hydroxide concentrations that could be used in the alkaline shock procedure. More specifically, the data revealed that use of the highest concentration of NaOH substantially compromised assay performance to the point where % positivity was reduced to zero. This amount of hydroxide solution, when mixed with the lysis/capture reagent and plasma sample, yielded a final pH of 12.6 (see Table 1). Thus, adding an amount of alkaline hydroxide sufficient to result in a final pH of 12.6 eliminated the ability of the assay to detect the target. Conversely, addition of an NaOH solution in an amount sufficient to raise the final pH to a range of from about 8.0 to about 10.6 gave good results. In this experiment, the best results were achieved by adding NaOH solution in an amount sufficient to raise the final pH to a range of from about 8.3 to about 8.8. Notably, this range was nearly identical to the preferred range of from pH 8.2 to 9.2 established in Example 8, below. These ranges define preferred pH ranges that result from the addition of appropriate amounts of an alkaline solution, preferably an alkaline hydroxide solution, to a buffered detergent solution containing a biological sample.

The following procedures proved that a transient high pH (i.e., an "alkaline shock") was required to achieve improved assay sensitivity. In this Example, the order in which three reagents were combined was varied to investigate whether the beneficial effects described herein resulted from changing the final pH of the sample, or from a different mechanism. Example 3 describes procedures which proved the beneficial effects of the alkaline shock method derive from a transient exposure to alkaline conditions.

EXAMPLE 3

A Transient Alkaline Shock is Required to Improve Assay Performance

Sample preparation methods that involved combining three reagents (an alkaline hydroxide, a plasma sample, and a lysis/capture reagent) in different orders were used to address the mechanism of action underlying the observed assay improvement. The reagents and their amounts used in the procedures were: 400 µl of lysis/capture reagent, 500 µl of a plasma sample containing HBV subtype-B virus particles (i.e., virus-infected plasma from a human donor diluted 1:10 with virus-negative processed plasma), and 100 µl of 1.6N NaOH. The concentration of the alkaline hydroxide solution was selected because it was within the range of those yielding good results in the preceding Example. All reagents were pipetted into plastic reaction tubes, and target-capture, amplification and detection were carried out as described in the preceding Examples. A control reaction conducted using 1:10 diluted HBV-positive plasma and lysis/capture reagent without any added NaOH gave 40% positive reactivity, thereby defining a standard for comparison. Negative control reactions conducted using HBV-negative plasma in place of the HBV-positive serum samples ("HBV Sample" in Table 2) for all of the conditions listed in the table uniformly gave 0% positive reactivity in the amplification and detection reaction, as expected. Procedures carried out using 1:20 diluted HBV-positive plasma samples in place of the 1:10 diluted samples gave results consistent with those presented in Table 3. The order of addition of the three reagents for each trial condition (n=10) is given in the table.

TABLE 3

A Transient Alkaline Shock Produces Beneficial Results

| First Reagent | Second Reagent | Third Reagent | % Positive |
|---|---|---|---|
| Lysis/Capture Reagent | HBV Sample | Alkali | 100 |
| Reagent | Alkali | HBV Sample | 20 |
| HBV Sample | Lysis/Capture Reagent | Alkali | 90 |
| | Alkali | Lysis/Capture Reagent | 100 |
| Alkali | Lysis/Capture Reagent | HBV Sample | 40 |
| | HBV Sample | Lysis/Capture Reagent | 80 |

The results in Table 3 indicated that the order of reagent addition profoundly influenced the assay outcome. First combining the lysis/capture reagent and alkaline hydroxide solution with each other, regardless of the order of addition of these reagents to the reaction tube, gave results similar to the control that omitted the alkaline shock. Thus, adding the virus-containing sample after the lysis/capture reagent and alkaline hydroxide were already combined yielded no benefit measurable by % positivity. Conversely, excellent results were achieved by first combining the lysis/capture reagent and the sample containing HBV virus particles (in either order), and thereafter combining the alkaline hydroxide solution with that mixture. This highly preferred order of addition advantageously avoided direct exposure of the biological sample to the concentrated hydroxide solution, and so advantageously should minimize alkaline hydrolysis of RNA templates.

While not wishing to be bound by any particular theory of operation, the foregoing results support a mechanism wherein a local, transient high pH within the reaction tube containing the lysis/capture reagent and virus sample had some effect which resulted in the advantages disclosed herein. Because success of the technique result from transient high pH exposure, the method disclosed herein has been termed, "alkaline shock."

The results presented above also indicated that the final pH of the reaction mixtures (as described in Example 1) can be used to gauge the amount of alkaline solution needed to produce good results, but that the final pH of the mixture did not predict success of the procedure. Indeed, if the final pH of the mixture determined the outcome of the assay, then all of the trial conditions presented in Table 3 would have yielded identical results, and that was not the case. Accordingly, preferred modes of carrying out the invention involve adding an alkaline solution to a sample that includes a pH buffer, a detergent and a biological sample to be tested for the presence of a particular nucleic acid. In a highly preferred embodiment, the biological sample is a body fluid, such as whole blood, plasma, serum, and the like.

The following Example employed a statistical analysis to measure how assay sensitivity for different HBV subtypes was improved by including an alkaline shock during the sample preparation procedure. For the purpose of this demonstration, a multiplex assay essentially as disclosed under Example 7 of published International Patent Application PCT/US03/18993, was employed with the only substantive difference being the addition of an alkaline shock step during the sample preparation procedure.

Example 4 describes how the alkaline shock technique improved quantitative assay performance for multiple HBV subtypes.

EXAMPLE 4

Quantifying Effects of the Alkaline Shock Technique

Figure 3A:
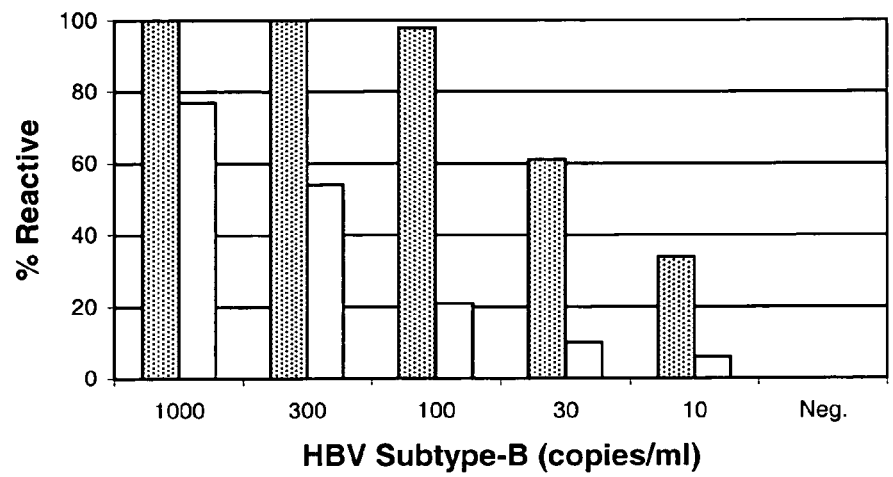
FIGS. 3A-3C are a series of bar graphs displaying results measured as % Reactive for different levels of input HBV virus.
Figure 3B:
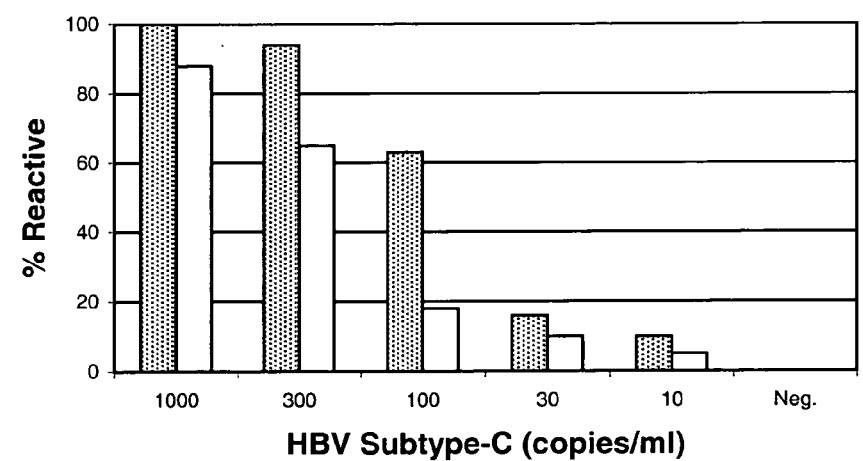
Figure 3C:
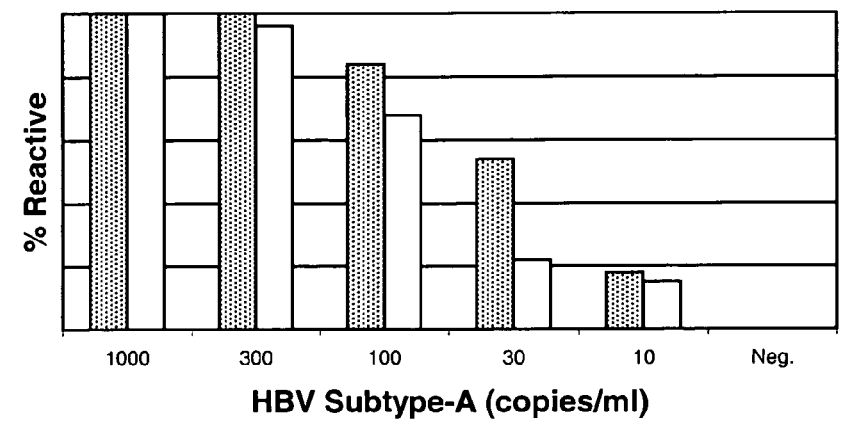

Panels of plasma samples containing known quantities of HBV subtype-A, -B or -C viral particles were produced by methods that will be familiar to those having an ordinary level of skill in the art. Samples were prepared using an alkaline shock protocol in which 400 μl of lysis/capture reagent and 500 μl of individual panel members were first combined in plastic reaction tubes, 100 μl of 1.6N NaOH was added, and the tubes agitated thereafter to ensure complete mixing. Target capture, amplification and detection of amplification products were carried out as described above. Control reactions that omitted the alkaline shock procedure were performed in parallel. Regression analysis using the Probit function in SAS® System software (version 8.02) (Cary, N.C.) was used to calculate the 95% and 50% detection levels. Invalid reactions were not re-tested and were not included in the analysis of analytical sensitivity. Results from these procedures are presented in FIGS. 3A-3C, and the Probit Analysis is summarized in Table 4.

TABLE 4

Quantifying the Effects of Alkaline Shock on HBV Subtype Detection

| HBV Genotype | Detection Probability | Assay Sensitivity (copies/ml) | | Fold Increase in Sensitivity |
|---|---|---|---|---|
| | | Control | Alkaline Shock | |
| B | 95% | 1405 (1168-1792) | 78 (61-116) | 18× |
| | 50% | 504 (440-623) | 22 (14-29) | 23× |
| C | 95% | 98 (78-134) | 26 (21-35) | 3.8× |
| | 50% | 37 (29-49) | 10 (8-13) | 3.7× |
| A | 95% | 74 (58-108) | 40 (32-57) | 1.9× |
| | 50% | 26 (20-34) | 12 (9-16) | 2.2× |

95% confidence intervals are shown in parentheses

The results summarized in Table 4 confirmed that the alkaline shock procedure enhanced detectability of all three subtypes of HBV, although to somewhat different extents. Using conventional procedures that did not employ an alkaline shock, assay sensitivity for the subtype-B virus at 95% detection probability was lower than the other subtypes by about 16 fold. Using the improved sample preparation method that incorporated an alkaline shock procedure prior to target capture and amplification dramatically improved assay performance to the point where all of the subtypes could be detected at levels below 100 copies/ml of sample. Interestingly, the alkaline shock sample preparation method improved assay sensitivity for the subtype-B virus most dramatically. This differential improvement could not have been predicted in advance of this showing, and may provide insight into the mechanism underlying the effect of the invented method.

Results presented in the preceding Examples showed that a transient alkaline shock during the sample preparation procedure dramatically improved subsequent detection of a nucleic acid target. Testing described in the following Example addressed the mechanism underlying this improvement. More specifically, an experiment was carried out to investigate whether addition of the alkaline hydroxide solution to the mixture of lysis/capture reagent and biological sample had only a denaturing effect on proteins and nucleic acids in the sample, thereby increasing availability of the viral nucleic acids for subsequent amplification and detection. Although alkaline conditions are known to denature proteins and nucleic acids, the results presented below indicated that the beneficial results observed by the procedures described herein were not fully explained by alkaline denaturation.

Example 5 describes procedures which proved that the alkaline shock phenomenon was not primarily mediated by alkaline denaturation of proteins and/or nucleic acids.

EXAMPLE 5

Alkaline Shock Requires the Combined Effects of Alkali and Detergent

Specialized lysis/capture reagents were prepared to contain either 0%, 5% or 10% lithium lauryl sulfate (LLS) detergent. Notably, all other instances of lysis/capture reagent described herein were prepared using 10% LLS. Aliquots (400 μl) of one of the target-capture reagents were first combined with aliquots (500 μl) of a 1:10 dilution of a serum sample obtained from a patient infected with HBV subtype-B. All trials included approximately 100 copies of the HBV genome. Thereafter, trials that were to be treated with alkaline hydroxide received 100 μl of 1.6 N NaOH, and were vortexed briefly. Control trials received 100 μl of water instead of NaOH solution. Target capture, amplification and detection of amplification products were carried out as described above. All trials were carried out in replicates of 10. Results from these procedures are presented in Table 5.

TABLE 5

Alkaline Shock Requires the Combination of a Detergent and Alkali

| % Detergent in Lysis/Capture Reagent | % Detection of HBV | |
|---|---|---|
| | Control | Alkaline Treatment |
| 0 | 0 | 0 |
| 5 | 10 | 80 |
| 10 | 20 | 90 |

The results presented in Table 5 indicated that the combination of detergent and alkali were required to effect the alkaline shock. Indeed, samples prepared using lysis/capture reagent that omitted detergent failed to detect the HBV analyte, even in trials that received the alkaline hydroxide. Thus, treatment with alkali in the absence of detergent under the specified pH conditions was not sufficient to yield good results. This indicated that the mechanism by which alkaline shock was effected was not entirely due to alkaline-mediated denaturation of proteins and nucleic acids. Instead, there was a synergistic effect that required first combining the biological sample with buffer and detergent, and thereafter adding the alkaline hydroxide.

In addition to procedures carried out using HBV particles as a model source of DNA targets, additional experiments were performed to investigate the effect of an alkaline shock during sample preparation on RNA targets. As in the preceding Example, a multiplex assay capable of amplifying and detecting HIV-1, HCV, and HBV nucleic acids was used to examine the effect of alkaline shock on RNA targets. Indeed, the known sensitivity of RNA to hydrolysis suggested that the alkaline shock procedure would only be useful in connection with the isolation of DNA targets preliminary to amplification and detection.

Example 6 describes procedures which demonstrated that RNA targets could be amplified and detected using nucleic acid templates prepared in procedures that included an alkaline shock.

EXAMPLE 6

Effect of Alkaline Shock on Detection of HIV-1 and HCV

Panels of plasma samples having known quantities of one of the following RNA viruses were produced by standard methods: HCV-1a, HCV-2b, and HIV-1b. Samples were prepared using an alkaline shock protocol in which 400 μl of lysis/capture reagent and 500 μl of individual panel members were first combined in plastic reaction tubes, 100 μl of 1.6N NaOH was added, and the tubes agitated thereafter to ensure complete mixing. Target capture, amplification and detection of amplification products were carried out essentially as described above, using appropriate detection probes at the conclusion of the amplification procedure. Control reactions that omitted the alkaline shock procedure were performed in parallel. Except for trials conducted using the highest viral titers, all reactions were performed using replicates of 20. Reactions conducted using the equivalent of 300 copies/ml of plasma sample were performed using replicates of 10. Results from these procedures are summarized in Tables 6-8, and in FIGS. 4A-4C. Table 9 presents results from a Probit Analysis of the data in Tables 6-8.

TABLE 6

Effect of Alkaline Shock on HCV-1a Amplification and Detection

| | HCV-1a Sample (RNA copies/ml) | % Positive | Number of Trials | Mean IC RLU | Mean Amplicon RLU | No. Invalid |
|---|---|---|---|---|---|---|
| Control | 300 | 100 | 10 | 185354 | 1453346 | 0 |
| | 100 | 100 | 20 | 182303 | 1368094 | 0 |
| | 30 | 95 | 20 | 185996 | 1165246 | 0 |
| | 10 | 52.6 | 20 | 199793 | 458035 | 1 |
| | 3 | 38.9 | 20 | 201781 | 352694 | 2 |
| Alkaline Shock | 300 | 100 | 10 | 162777 | 1398738 | 0 |
| | 100 | 100 | 20 | 170729 | 1411556 | 0 |
| | 30 | 95 | 20 | 170932 | 1157907 | 0 |
| | 10 | 75 | 20 | 179854 | 865606 | 0 |
| | 3 | 46.7 | 20 | 182010 | 530033 | 5 |

TABLE 7

Effect of Alkaline Shock on HCV-2b Amplification and Detection

| | HCV-2b Sample (RNA copies/ml) | % Positive | Number of Trials | Mean IC RLU | Mean Amplicon RLU | No. Invalid |
|---|---|---|---|---|---|---|
| Control | 300 | 100 | 10 | 265152 | 1272494 | 0 |
| | 100 | 100 | 20 | 251077 | 1190681 | 0 |
| | 30 | 95 | 20 | 241570 | 911405 | 0 |
| | 10 | 73.7 | 20 | 236737 | 514461 | 0 |
| | 3 | 15 | 20 | 235306 | 67760 | 1 |
| Alkaline Shock | 300 | 100 | 10 | 242148 | 1287926 | 0 |
| | 100 | 100 | 20 | 260091 | 1020347 | 0 |
| | 30 | 90 | 20 | 246163 | 530746 | 0 |

TABLE 7-continued

Effect of Alkaline Shock on HCV-2b Amplification and Detection

| HCV-2b Sample (RNA copies/ml) | % Positive | Number of Trials | Mean IC RLU | Mean Amplicon RLU | No. Invalid |
|---|---|---|---|---|---|
| 10 | 55 | 20 | 232982 | 244802 | 0 |
| 3 | 5.3 | 20 | 224816 | 43514 | 1 |

TABLE 8

Effect of Alkaline Shock on HIV-1b Amplification and Detection

| | HIV-1b Sample (RNA copies/ml) | % Positive | Number of Trials | Mean IC RLU | Mean Amplicon RLU | No. Invalid |
|---|---|---|---|---|---|---|
| Control | 300 | 100 | 10 | 11883 | 35509 | 0 |
| | 100 | 100 | 20 | 11824 | 103981 | 0 |
| | 30 | 100 | 20 | 22536 | 179092 | 1 |
| | 10 | 80 | 20 | 7814 | 115883 | 0 |
| | 3 | 40 | 20 | 4167 | 52622 | 0 |
| Alkaline Shock | 300 | 100 | 10 | 11738 | 19499 | 0 |
| | 100 | 100 | 20 | 13823 | 110696 | 0 |
| | 30 | 90 | 20 | 10468 | 166067 | 0 |
| | 10 | 68 | 20 | 22082 | 169677 | 1 |
| | 3 | 21 | 20 | 21784 | 53292 | 1 |

Figure 4A:
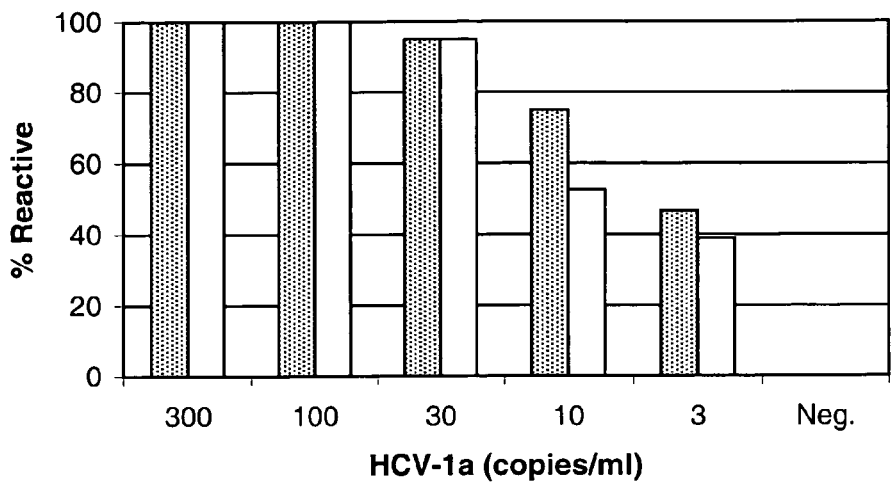
FIGS. 4A-4C are a series of bar graphs displaying results measured as % Reactive for different levels of input RNA viruses.
Figure 4B:
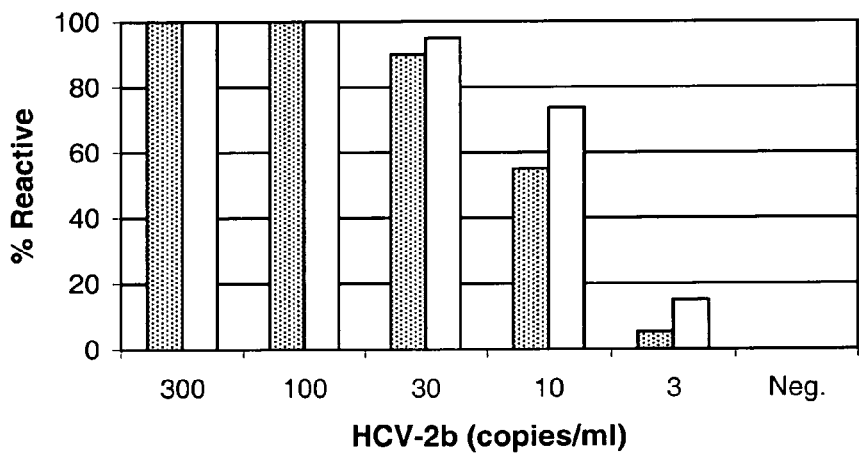
Figure 4C:
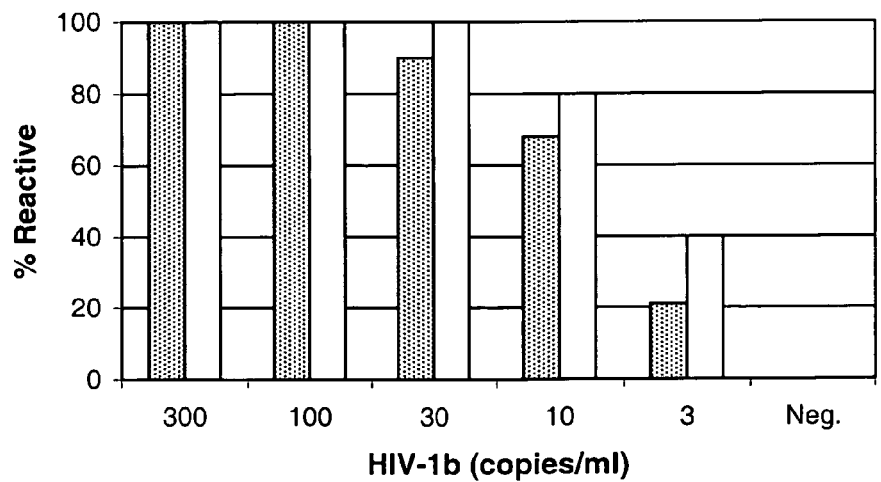

The results presented in Tables 6-8, and in FIGS. 4A-4C indicated that any effect of the alkaline shock treatment of samples being tested for the presence of RNA viruses was very minor. For instance, assay sensitivity for HCV-1a appeared to increase slightly, while the sensitivity for HCV-2b and HIV-1b may have decreased slightly. Notably, it is unclear whether these differences, which were noted only at very low viral titers, were statistically significant. Overall, the results confirmed that an alkaline shock could be integrated into a single sample preparation procedure for isolating RNA and DNA targets. It was somewhat surprising that the treatment could be gentle enough to permit subsequent detection of RNA targets while being adequate to provide substantial enhancement of DNA targets.

TABLE 9

Quantifying the Effects of Alkaline Shock on Detection of RNA Targets

| RNA Taret | Detection Probability | Assay Sensitivity (copies/ml) | |
|---|---|---|---|
| | | Control | Alkaline Shock |
| HCV-1a | 95% | 32 (22-69) | 28 (18-93) |
| | 50% | 8 (0-13) | 3 (0-8) |
| HCV-2b | 95% | 23 (16-52) | 31 (23-54) |
| | 50% | 8 (4-13) | 13 (8-19) |
| HIV-1b | 95% | 16 (11-42) | 32 (23-65) |
| | 50% | 5 (0-8) | 9 (3-15) |

95% confidence intervals are shown in parentheses

The tabulated results from the Probit Analysis, presented in Table 9, indicated that the alkaline shock treatment did not substantially impair detectability of the RNA targets. Thus, the same alkaline shock conditions that enhanced detection of the HBV subtype-B nucleic acid did not substantially compromise detection of RNA targets.

The foregoing Example demonstrated that sample preparation procedures which incorporated an alkaline shock could be used to isolate RNA templates, in addition to DNA templates. This result was somewhat surprising because RNA is known to be subject to hydrolysis under alkaline conditions. The following Example confirmed this susceptibility when the sample preparation procedure was varied such that a biological sample containing a known amount of HIV-O virions was first combined with an alkaline hydroxide prior to addition of a pH buffer and detergent.

Example 7 describes procedures that were followed to assess the effect of alkaline treatment on the integrity of an RNA target. Results from these procedures showed that RNA hydrolysis was very rapid following contact between the biological sample containing HIV-O virions and the alkaline hydroxide solution.

EXAMPLE 7

Order of Reagent Addition Profoundly Affects RNA Integrity

Serum samples containing HIV-O virions were diluted to known titers using virus-negative serum. Aliquots (500 μl) of virion-containing serum (i.e., containing 30 copies/ml) were first deposited into plastic reaction tubes. Thereafter, 100 μl aliquots of 1.8 N LiOH were added and the tubes allowed to stand for variable periods of time. Next, an aliquot (400 μl) of lysis/capture reagent was added and vortexed briefly. The delay time between addition of the alkaline hydroxide solution and the pH buffered detergent solution (i.e., the lysis/capture reagent) ranged from 0 minutes to 1 hour. Surviving RNA templates were captured, amplified, and detected essentially as described above. Notably, the pH-buffered lysis/capture reagent in this procedure included a synthetic HIV-1 transcript that served as the internal amplification control. All trials were conducted in replicates of 10.

TABLE 10

Assessing the Effect of Alkali on RNA Integrity

| Sample | Time Delay (mins) | % CV IC RLU | # Trials | # Invalid | % Positive |
|---|---|---|---|---|---|
| Neg. Serum | 0 | 13 | 10 | 0 | 0 |
| HIV-O | 0 | 5 | 10 | 0 | 10 |
| 30 copies/ml | 2.5 | 9 | 10 | 0 | 0 |
| | 5 | 3 | 10 | 0 | 0 |

The results presented in Table 10 indicated that hydrolysis of the HIV-O RNA target was very rapid when the alkaline hydroxide solution was added to the biological sample in the absence of a pH buffer. Notably, results from preliminary testing indicated that the HIV-O target was detected at 100% efficiency at the 30 copy/ml level when the alkaline hydroxide was either omitted from the procedure or added after the virus-containing sample was first combined with the lysis/capture reagent (i.e., a pH buffered detergent solution). As indicated in the table, only one of ten replicates yielded detectable RNA templates when virus-containing serum was mixed with the alkaline hydroxide solution and immediately thereafter neutralized by the addition of lysis/capture reagent which included a pH buffer. Other time points which extended the delay between addition of the pH buffered solution to the alkali-treated virus samples by up to one hour also yielded no detectable RNA templates, and so have been omitted from the table. The fact that the RNA internal control survived the procedure, as judged by the fact that all of the trials were considered valid, was expected. Taken together, these results confirmed that mixing a biological sample containing an RNA target with an alkaline hydroxide solution prior to addition of a pH buffer completely compromised the integrity of the RNA template. On the other hand, first combining the RNA template with a pH buffer prior to mixing with the alkaline hydroxide solution preserved template integrity.

Given the showing that RNA and DNA targets could be detected in multiplex assays using a shared sample preparation method that incorporated an alkaline shock, it was of interest to explore more fully the effect of pH during the sample preparation procedure on final assay performance. As indicated below, when the amount of alkaline hydroxide used in the sample preparation procedure resulted in a final pH greater than 9.5, the assay performed poorly. Notably, the procedures described in the following Example employed LiOH in place of NaOH to effect the alkaline shock, and so also illustrated that the identity of the alkaline hydroxide used in the procedure was not critical for success of the sample preparation method.

Example 8 describes procedures that were followed to determine the upper limit of the useful pH range for performing alkaline shock-based sample preparation procedures.

EXAMPLE 8

Optimizing the Amount of Alkaline Hydroxide Used for Conducting the Alkaline Shock Biological samples containing RNA or DNA viral targets were tested in the model multiplex assay to determine how assay performance was influenced by the final pH of a mixture that included a virus-containing plasma or serum sample, a buffered detergent solution (i.e., a lysis/capture reagent), and an alkaline hydroxide during the sample preparation procedure. In this procedure, 1.9 N LiOH was used in place of 1.6 N NaOH to effect the alkaline shock. Preliminary procedures to determine the final pH that resulted from the addition of different amounts of the LiOH solution were conducted in replicates of three, and the pH averages determined from those readings. In these preliminary procedures, 400 μl of lysis/capture reagent was combined with 500 μl of virus-negative serum and different volumes of 1.9N LiOH, and the final pH of the mixtures determined as described above. The biological samples tested were: (1) HIV-1 O group positive plasma containing the equivalent of 30 copies/ml of the viral RNA; (2) HCV-1a positive plasma containing the equivalent of 30 copies/ml of the viral RNA; and (3) HBV subtype B diluted into virus-negative control serum to a level of less than 200 copies/ml. Virus-negative serum served as a control in the procedure. In all instances, the biological sample was first combined with the lysis/capture reagent, and an aliquot of the alkaline hydroxide solution added and mixed thereafter. The number of valid and invalid runs was scored following the amplification and detection procedure, and the positively reacting trials determined as a percentage of the valid runs. All reactions were conducted using replicates of ten. A separate procedure involved essentially similar methods, but focused on the addition of LiOH in amounts that resulted in a slightly different pH range during the sample preparation step, and tested HBV subtype B-containing serum samples, HBV subtype C-containing serum samples, and HIV-1 O group positive plasma. The results from these procedures are summarized in Tables 11 and 12.

TABLE 11

Establishing the Upper Limit of a Useful pH Range

| Sample | Vol. 1.9 N LiOH (μl) | % pos | No. Invalid | No. Valid | No. Reactive | Avg. pH (n = 3) |
|---|---|---|---|---|---|---|
| HIV-1 O group | 100 | 100 | 0 | 10 | 10 | 8.6 |
| HCV-1a |  | 100 | 0 | 10 | 10 |  |
| HBV-B |  | 100 | 0 | 10 | 10 |  |
| Neg. Serum |  | 0 | 0 | 10 | 0 |  |
| HIV-1 O group | 120 | 100 | 2 | 8 | 8 | 9.2 |
| HCV-1a |  | 100 | 3 | 7 | 7 |  |
| HBV-B |  | 100 | 2 | 8 | 8 |  |
| Neg. Serum |  | 0 | 0 | 10 | 0 |  |
| HIV-1 O group | 122.5 | 75 | 2 | 8 | 6 | 9.5 |
| HCV-1a |  | 88 | 1 | 9 | 8 |  |
| HBV-B |  | 100 | 2 | 8 | 8 |  |
| Neg. Serum |  | 0 | 5 | 5 | 0 |  |
| HIV-1 O group | 125 | 0 | 8 | 1 | 0 | 10.7 |
| HCV-1a |  | 0 | 10 | 0 | 0 |  |
| HBV-B |  | 100 | 7 | 3 | 3 |  |
| Neg. Serum |  | 0 | 8 | 2 | 0 |  |

TABLE 12

Establishing the Upper Limit of a Useful pH Range

| Sample | Vol. 1.9 N LiOH (μl) | % pos | No. Invalid | No. Valid | Avg. pH (n = 3) |
|---|---|---|---|---|---|
| HBV-B | 70 | 100 | 0 | 10 | 8.02 |
|  | 85 | 100 | 0 | 10 | 8.22 |
|  | 100 | 90 | 0 | 10 | 8.46 |
|  | 115 | 100 | 0 | 10 | 8.73 |
|  | 130 | none | 10 | 0 | 10.08 |
| HBV-C | 70 | 60 | 0 | 10 | 8.02 |
|  | 85 | 70 | 0 | 10 | 8.22 |
|  | 100 | 100 | 0 | 10 | 8.46 |
|  | 115 | 100 | 0 | 10 | 8.73 |
|  | 130 | none | 10 | 0 | 10.08 |
| HIV-1 O group | 70 | 80 | 0 | 10 | 8.02 |
|  | 85 | 90 | 0 | 10 | 8.22 |
|  | 100 | 70 | 0 | 10 | 8.46 |
|  | 115 | 80 | 0 | 10 | 8.73 |
|  | 130 | none | 10 | 0 | 10.08 |

The results presented in Table 11 confirmed that HBV could be detected at all pH levels tested, and established the upper limit of a useful pH range for assays that included an RNA analyte or RNA internal control. More specifically, Table 11 shows that reactions conducted using HBV subtype-B as the target gave 100% detectability in valid reactions at all levels of added alkaline hydroxide. However, the number of reactive trials dropped below one-half under the highest pH condition for the HBV analyte. Thus, it is less preferred to conduct alkaline shock-based sample preparation when the amount of added alkaline hydroxide causes the pH to exceed pH 10, and when the method includes a step for capturing analyte nucleic acids preliminary to amplification. Assays designed to detect RNA targets, or that rely on controls or calibrators that include RNA showed a distinctly different sensitivity to the pH conditions when compared with the results using the DNA target. When the amount of alkaline hydroxide used to effect the alkaline shock resulted in a mixture having a final pH of 9.5 or greater, the number of invalid runs increased dramatically when compared with the results of trials performed using final pH conditions of 9.2 and lower. Moreover, the % positive results indicated that trials conducted using the HIV-1 O group and HCV-1a RNA targets were detected in 100% of reactions yielding valid results when the final pH of the mixture was 9.2 or lower. The % positive values dropped somewhat when the final pH was 9.5, and were fully compromised when the final pH was 10.7. While not wishing to be bound by any particular theory of operation, these results were consistent with a decrease in the efficiency of capturing intact targets for subsequent amplification when the final pH exceeded about pH 9.5.

The results presented in Table 12 indicated that all runs were valid, and that good results were achieved when the amount of alkaline hydroxide added to a mixture of biological sample and buffered detergent solution (i.e., lysis/capture reagent) was sufficient to result in a pH falling in the range of from about pH 8.0 up to less than about pH 10. Excellent results were achieved when the amount of added alkaline hydroxide was sufficient to result in a pH falling in the range of from about pH 8.0 up to about pH 8.7. The procedures that yielded the results appearing in Table 12 did not clearly establish the upper limit of alkaline hydroxide that could be used to effect the alkaline shock. That determination was made based on the results in Table 11.

Based on the aggregated results presented herein, there was a preferred upper limit to the pH of a mixture that included a buffered detergent solution (i.e., a lysis/capture reagent), a biological sample (such as a sample of blood, plasma or serum), and an alkaline hydroxide. More particularly, the amount of alkaline hydroxide used in the mixture preferably yields a final pH of at least pH 8.0, but should not exceed about pH 10.0. More preferably, and especially when RNA targets are to be captured and amplified, the amount of alkaline hydroxide used in the mixture preferably should yield a final pH of at least pH 8.0 but less than pH 9.5. Still more preferably, the amount of alkaline hydroxide used in the mixture preferably should yield a final pH of at least pH 8.0, but should be equal to or less than about pH 9.2 (i.e., a final pH in the range of pH 8.0-9.2). Still more preferably, the amount of alkaline hydroxide used in the mixture preferably should yield a final pH of at least pH 8.0 but equal to or less than about pH 8.73 (i.e., a final pH in the range of pH 8.0-8.73). Yet still more preferably, the amount of alkaline hydroxide used in the mixture preferably should yield a final pH of at least pH 8.0 but equal to or less than about pH 8.6 (i.e., a final pH in the range of pH 8.0-8.6). In all instances, it was preferred for the combination of the biological sample, the buffer, and the detergent (i.e., prior to addition of the alkaline composition used to effect the alkaline shock) to have a pH falling in the range of from 6.5 to 8.0, more preferably in the range of from pH 7.0 to 8.0, more preferably in the range of from 7.0 to about 7.5. Indeed, when the combination of the biological sample, the buffer, and the detergent yielded a pH falling in the range of from pH 6.5-8.0, when the addition of the alkaline composition to effect the alkaline shock produced an increase of at least 0.2 pH units, and when the final pH of the mixture following the alkaline shock fell in the range of from pH 8.2 to 9.2, excellent results were achieved for preparation of both DNA and RNA templates.

The foregoing demonstrations focused on the benefits of using the alkaline shock technique during the preparation of nucleic acids from RNA and DNA viruses. The following Example describes how the same alkaline shock technique has been extended to the preparation of nucleic acids from bacteria. In this illustration, nucleic acids were prepared from *Streptococcus agalactiae*, a member of the Group B *Streptococci* (GBS). Those having an ordinary level of skill in the art will appreciate that GBS bacteria are known to be difficult to lyse. Thus, the illustration presented below represents a stringent test of the alkaline shock sample preparation method, and can be taken as indicating that the technique is useful for preparing nucleic acids from any bacterial species.

Example 9 details procedures that were used to prepare and detect nucleic acids from bacteria. The procedure included a fully integrated lysis, target capture, amplification and detection protocol conducted with and without the alkaline shock step. This isolated the effect of the alkaline shock procedure with respect to the preparation of nucleic acid templates from bacteria. In vitro amplification was carried out using a Transcription Mediated Amplification (TMA) protocol.

EXAMPLE 9

Preparation and Detection of Bacterial Nucleic Acids

Cultured *S. agalactiae* bacteria were employed for testing the efficiency of sample preparation using the alkaline shock technique. Bacteria grown overnight in a liquid culture medium were collected by gentle centrifugation, and then washed 10 times in PBS to remove residual traces of nucleic acids that may have been released into the culture medium. The resulting bacterial pellet was taken up in PBS and then serially diluted. Aliquots of the different dilutions were spread onto blood agar plates to determine accurate titers. Remaining portions of the samples were used for preparing nucleic acids with and without alkaline shock, and the prepared samples used as sources of nucleic acid templates in TMA amplification reactions. Aliquots (400 µl) of a lysis/capture reagent containing 4 pmols of a capture oligonucleotide having SEQ ID NO:1, together with about 40 µg 0.7-1.05 µ paramagnetic particles (Seradyn, Indianapolis, Ind.) covalently linked to poly-($dT_{14}$) were combined with aliquots (500 µl) of diluted GBS containing known numbers of organisms in plastic reaction tubes. The capture oligonucleotides were capable of simultaneously hybridizing to the particle-bound poly-(dT) and to the bacterial rRNA. Samples were prepared in replicates of nine for each level of bacteria undergoing testing. Control tubes included with each set included 500 µl of PBS containing 1,000 copies of purified bacterial rRNA instead of bacterial cells. Each tube then received 100 µl of either a water control, or 1.6 N NaOH to effect the alkaline shock. After vortexing for 10 seconds, the mixtures were incubated at 60° C. in a water bath for 15 minutes, followed by incubation at room temperature for another 15 minutes to allow hybridization and target capture onto the magnetic particles. As described above, a magnetic field was applied to collect the particle complexes containing the immobilized capture oligonucleotide and rRNA, and the collected particles washed twice with 1 ml of a washing buffer. Washed particles were resuspended in 75 µl of an amplification reagent, and the contents of the tube overlaid with inert oil to prevent evaporation. As above, the amplification reagent included salts, nucleotides, ribonucleotides and about 5 pmol/reaction each of two rRNA-specific primers having the sequences of SEQ ID NO:3 and SEQ ID NO:2. After vortexing briefly, the mixture was incubated at 60° C. for 10 minutes to facilitate primer annealing, and then equilibrated at 41.5° C. for 10 minutes. Aliquots of pre-warmed enzyme reagent that included Moloney Murine Leukemia Virus (MMLV) reverse transcriptase (5,600 units/reaction) and T7 RNA polymerase (3,500 units/reaction) were then added to the mixtures. After a one hour incubation at 41.5° C., the reaction was complete and rRNA amplification products were detected in a standard homogenous protection assay, essentially as described under Example 1 of published International Patent Application No. PCT/US03/18993 using an acridinium ester-labeled hybridization probe having the sequence of SEQ ID NO:4. The sequences of the relevant oligonucleotides employed for amplifying and detecting GBS bacteria appear in Table 13.

TABLE 13

Oligonucleotides for Detecting a Bacterial Target Nucleic Acid

| Oligo Function | Oligo Sequence | Oligo Identifier |
|---|---|---|
| Target Capture | GUUACGGGGCCAUUUUGCCGAGUUCCTTTA AAAAAAAAAAAAAAAAAAAAAAAAAAAAA | SEQ ID NO:1 |
| T7 promoter-primer | AATTTAATACGACTCACTATAGGGAGAGACT ACCTGTGTCGGTTTGCGGT | SEQ ID NO:2 |
| non-T7 primer | GCGAAGTTTAGTAGCGAAGTTAGTGATGT | SEQ ID NO:3 |
| Probe | GCUUCUAGCGAUACAUAUACUCUACCC | SEQ ID NO:4 |

Figure 5:
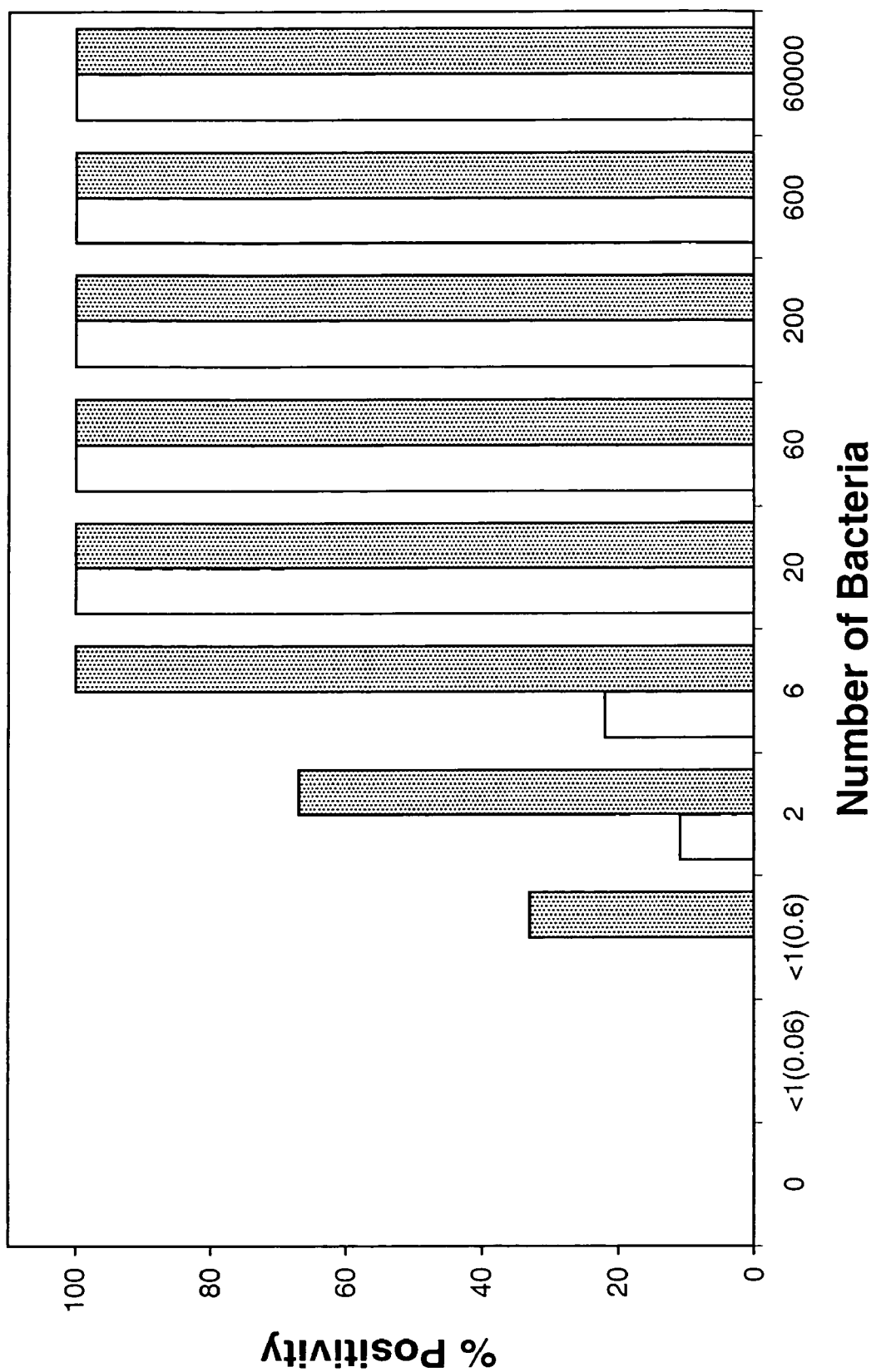
FIG. 5 shows a series of bar graphs displaying % positivity determined in amplification reactions using template nucleic acids isolated from different numbers of GBS bacteria. Trials employing nucleic acid templates processed without an alkaline shock are indicated by open bars. Trials employing nucleic acid templates processed with an alkaline shock are indicated by filled bars.

The results presented in FIG. 5 confirmed that the sample preparation procedure which included an alkaline shock yielded dramatically improved results over standard procedures. In every case, samples were judged as positive if the chemiluminescent signal indicating detection of rRNA amplicons exceeded the signal detected in control trials conducted using 1000 copies of the rRNA template. As indicated in the figure, trials conducted using at least 20 GBS bacteria as the source of nucleic acid templates uniformly gave positive results, regardless of whether the alkaline shock was included in the sample preparation procedure. However, while the standard sample preparation procedure was useful for reliably detecting as few as about 10 GBS bacteria when used in conjunction with an in vitro amplification and detection assay, the procedure that included the alkaline shock could be used for reliably detecting as few as a single bacterium. These conclusions are based on a statistical analysis, where, among a collection of replicate samples receiving an aliquot intended to contain one bacterium some samples will contain none and some samples will contain two bacteria. Clearly, the alkaline shock sample preparation procedure dramatically improved detection of the bacterial target nucleic acid.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A method of processing a biological sample, comprising the steps of:
   (a) combining said biological sample with a pH buffer and a detergent that lyses or disrupts biological membranes that may be present in said biological sample, whereby there is created a first liquid composition having a first pH;
   (b) mixing with said first liquid composition an alkaline composition, whereby there is created a second liquid composition having a second pH,
      wherein said alkaline composition is a solution comprising a strong base at a concentration of at least 0.1 N;
      wherein said second pH is at least 0.2 pH units higher than said first pH, and
      wherein said second pH is lower than pH 9.5;
   (c) capturing one or more nucleic acids from said second liquid composition onto a solid support; and
   (d) isolating the solid support having captured thereon any of said one or more nucleic acids.

2. The method of claim 1, wherein said pH buffer and said detergent in step (a) are each components of a buffered detergent solution, and wherein the combining step comprises combining said biological sample with an aliquot of said buffered detergent solution.

3. The method of claim 1, wherein said second pH is in the range of from pH 8.0 to pH 9.2.

4. The method of claim 3, wherein at least one of said one or more nucleic acids captured in step (c) comprises an RNA molecule.

5. The method of claim 3, wherein at least one of said one or more nucleic acids captured in step (c) comprises a DNA molecule.

6. The method of claim 3, wherein said first pH is in the range of from 6.5 to 8.0.

7. The method of claim 3, wherein step (c) comprises hybridizing said one or more nucleic acids to one or more immobilized or immobilizable oligonucleotides complementary thereto.

8. The method of claim 7, wherein said pH buffer and said detergent in step (a) are each components of a buffered detergent solution, and wherein the combining step comprises combining said biological sample with an aliquot of said buffered detergent solution.

9. The method of step 8, wherein said buffered detergent solution further comprises said one or more immobilized or immobilizable oligonucleotides.

10. The method of claim 1, wherein said first pH is in the range of from 6.5 to 8.0.

11. The method of claim 10, wherein step (c) comprises hybridizing said one or more nucleic acids to one or more immobilized or immobilizable oligonucleotides complementary thereto.

12. The method of claim 11, wherein said pH buffer and said detergent in step (a) are each components of a buffered detergent solution, and wherein the combining step comprises combining said biological sample with an aliquot of said buffered detergent solution.

13. The method of step 12, wherein said buffered detergent solution further comprises said one or more immobilized or immobilizable oligonucleotides.

14. The method of claim 13, wherein step (d) comprises separating the solid support from material not captured thereon, and then washing the solid support having captured thereon any of said one or more nucleic acids.

15. The method of claim 14, wherein each of steps (a)-(d) is carried out in a single reaction vessel.

16. The method of claim 1, wherein step (c) comprises hybridizing said one or more nucleic acids to one or more immobilized or immobilizable oligonucleotides complementary thereto.

17. The method of claim 16, wherein said pH buffer and said detergent in step (a) are each components of a buffered detergent solution, and wherein the combining step comprises combining said biological sample with an aliquot of said buffered detergent solution.

18. The method of step 17, wherein said buffered detergent solution further comprises said one or more immobilized or immobilizable oligonucleotides.

19. The method of claim 1, wherein said detergent is selected from the group consisting of an anionic detergent and a non-ionic detergent.

20. The method of claim 19, wherein said strong base is selected from the group consisting of NaOH and LiOH.

21. The method of claim 1, wherein each of steps (a)-(d) is carried out in a single reaction vessel.

22. The method of claim 21, wherein step (b) comprises either (i) agitating by orbital shaking or (ii) vortexing.

23. The method of claim 1, wherein said solid support comprises a bead.

24. The method of claim 23, wherein said bead is a magnetic bead.

25. The method of claim 1, wherein the pKa of said pH buffer is between 6.0 and 9.0.

26. The method of claim 1, wherein at least one of said one or more nucleic acids captured in step (c) comprises an RNA molecule.

27. The method of claim 1, wherein at least one of said one or more nucleic acids captured in step (c) comprises a DNA molecule.

28. The method of claim 1, wherein said first pH is in the range of from pH 6.5 to 8.0, and wherein said second pH is in the range of from pH 8.2 to 9.2.

29. The method of claim 1, further comprising the step of:
(e) performing an in vitro nucleic acid amplification reaction using as a template at least one of said one or more nucleic acids captured on the solid support isolated in the step (d).

30. The method of claim 29, wherein said second pH is in the range of from pH 8.0 to pH 9.2.

31. The method of claim 30, wherein said first pH is in the range of from 6.5 to 8.0.

32. The method of claim 29, wherein said first pH is in the range of from 6.5 to 8.0.

33. The method of claim 32, wherein said second pH is in the range of from pH 8.2 to 9.2.

34. The method of claim 29, wherein said in vitro nucleic acid amplification reaction is a multiplex reaction.

35. The method of claim 34, wherein said one or more nucleic acids captured in step (c) comprise two or more captured nucleic acids, wherein said one or more nucleic acids isolated in step (d) comprise two or more isolated nucleic acids, and wherein said multiplex reaction uses as templates two of said two or more nucleic acids that were captured in step (c) and then isolated step (d).

36. The method of claim 35, wherein said two nucleic acids used as templates in said multiplex reaction comprise an RNA molecule and a DNA molecule.

37. The method of claim 29, wherein each of steps (a)-(e) is carried out in a single reaction vessel.

38. The method of claim 37, wherein step (b) comprises either (i) agitating by orbital shaking or (ii) vortexing.

* * * * *

UNITED STATES PATENT AND TRADEMARK OFFICE
CERTIFICATE OF CORRECTION

PATENT NO. : 7,510,837 B2 Page 1 of 1
APPLICATION NO. : 11/356613
DATED : March 31, 2009
INVENTOR(S) : Kui Gao et al.

It is certified that error appears in the above-identified patent and that said Letters Patent is hereby corrected as shown below:

Claim 9, Column 33, Line 63: delete "step" and insert --claim--;

Claim 13, Column 34, Line 25: delete "step" and insert --claim--; and

Claim 18, Column 34, Line 43: delete "step" and insert --claim--.

Signed and Sealed this

Fourteenth Day of July, 2009

JOHN DOLL
*Acting Director of the United States Patent and Trademark Office*

SEQUENCE LISTING

<160> NUMBER OF SEQ ID NOS: 4

<210> SEQ ID NO 1
<211> LENGTH: 59
<212> TYPE: DNA
<213> ORGANISM: Streptococcus agalactiae
<220> FEATURE:
<221> NAME/KEY: misc_feature
<222> LOCATION: (1)..(26)
<223> OTHER INFORMATION: Sequence complementary to rRNA
<220> FEATURE:
<221> NAME/KEY: misc_structure
<222> LOCATION: (1)..(26)

<400> SEQUENCE: 1
guuacggggc cauuuugccg aguuccttta aaaaaaaaaa aaaaaaaaaa aaaaaaaa        59

<210> SEQ ID NO 2
<211> LENGTH: 50
<212> TYPE: DNA
<213> ORGANISM: Streptococcus agalactiae

<400> SEQUENCE: 2
aatttaatac gactcactat agggagagac tacctgtgtc ggtttgcggt                 50

<210> SEQ ID NO 3
<211> LENGTH: 29
<212> TYPE: DNA
<213> ORGANISM: Streptococcus agalactiae

<400> SEQUENCE: 3
gcgaagttta gtagcgaagt tagtgatgt                                         29

```
<210> SEQ ID NO 4
<211> LENGTH: 27
<212> TYPE: DNA
<213> ORGANISM: Streptococcus agalactiae
<220> FEATURE:
<221> NAME/KEY: misc_structure
<222> LOCATION: (1)..(27)
<223> OTHER INFORMATION: 2' methoxy backbone

<400> SEQUENCE: 4
gcuucuagcg auacauauac ucuaccc                                              27
```